(12) United States Patent
Bode et al.

(10) Patent No.: US 9,616,047 B2
(45) Date of Patent: Apr. 11, 2017

(54) INHIBITORS OF BETA-CATENIN IN TREATMENT OF COLORECTAL CANCER

(71) Applicant: Regents of the University of Minnesota, Minneapolis, MN (US)

(72) Inventors: Ann Marie Bode, Cannon Falls, MN (US); Zigang Dong, Austin, TX (US); Srinivasa Reddy Kanamata Reddy, Austin, TX (US)

(73) Assignee: Regents of University of Minnesota, Minneapolis, MN (US)

( * ) Notice: Subject to any disclaimer, the term of this patent is extended or adjusted under 35 U.S.C. 154(b) by 0 days.

(21) Appl. No.: 14/788,373

(22) Filed: Jun. 30, 2015

(65) Prior Publication Data

US 2015/0374662 A1     Dec. 31, 2015

Related U.S. Application Data

(60) Provisional application No. 62/019,252, filed on Jun. 30, 2014.

(51) Int. Cl.
*A61K 31/404* (2006.01)
*A61K 31/4184* (2006.01)
*A61K 31/454* (2006.01)
*A61K 31/4545* (2006.01)
*C07D 209/34* (2006.01)
*C07D 209/38* (2006.01)

(52) U.S. Cl.
CPC ........ *A61K 31/404* (2013.01); *A61K 31/4184* (2013.01); *A61K 31/454* (2013.01); *A61K 31/4545* (2013.01); *C07D 209/34* (2013.01); *C07D 209/38* (2013.01)

(58) Field of Classification Search
None
See application file for complete search history.

(56) References Cited

U.S. PATENT DOCUMENTS

2011/0275645 A1    11/2011    Desai et al.

FOREIGN PATENT DOCUMENTS

| CN | 1365972 A | | 8/2002 |
| WO | WO 2009/029609 | * | 3/2009 |
| WO | WO-2010083505 A1 | | 7/2010 |

OTHER PUBLICATIONS

Berezov, A., et al., "Disabling the mitotic spindle and tumor growth by targeting a cavity-induced allosteric site of survivin", NIH Public Access, Author Manuscript, published in final edited form as: Oncogene, 31(15), (2012), 1938-1948, (2012), 18 pgs.

Cong, Feng, et al., "A protein knockdown strategy to study the function of beta-catenin in tumorigenesis", BMC Mol Biol., 4:10, (2003), 11 pgs.

Ilyas, M., et al., "Beta-catenin mutations in cell lines established from human colorectal cancers", Proc. Natl. Acad. Sci. USA, 94(19), (Sep. 1997), 10330-10334.

Lepourcelet, Maina, et al., "Small molecule antagonists of the oncogenic Tcf/beta-catenin protein complex", Cancer Cell, 5(1), (2004), 91-102.

Sadot, Einat, et al., "Down-regulation of beta-catenin by activated p53", Mol Cell Biol., 21(20), (2001), 6768-6781.

Saito, Hiroaki, et al., "Synthesis of methoxy- and bromo-substituted indirubins and their activities on apoptosis induction in human neuroblastoma cells", Bioorganic & Medicinal Chemistry Letters, 21, (2011), 5370-5373.

\* cited by examiner

*Primary Examiner* — Samantha Shterengarts
(74) *Attorney, Agent, or Firm* — Schwegman, Lundberg & Woessner, P.A.

(57) ABSTRACT

Compounds are disclosed which are effective for inhibiting β-catenin or disrupting a β-catenin/Tcf-4 complex, and for causing effective attenuation of colon carcinogenesis. The compounds may be effective treatment for colorectal cancer (CRC) when administered in an effective dose to a patient afflicted therewith.

10 Claims, 10 Drawing Sheets

Figure 1
HI-B1, HI-B5 and HI-B9 inhibit beta-catenin/TCF4 transcriptional activity in colon cancer cell lines.
A
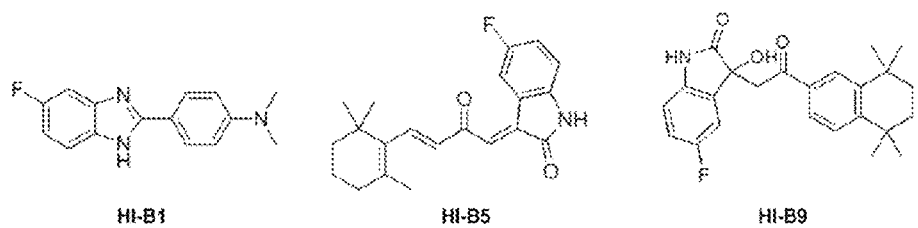
B
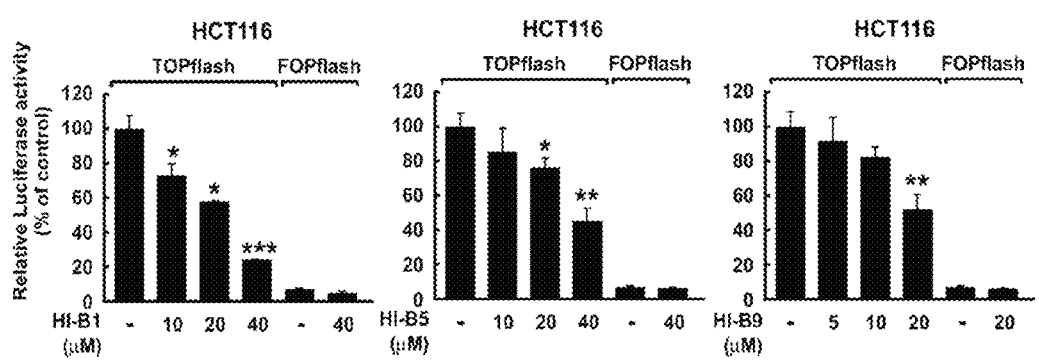
C
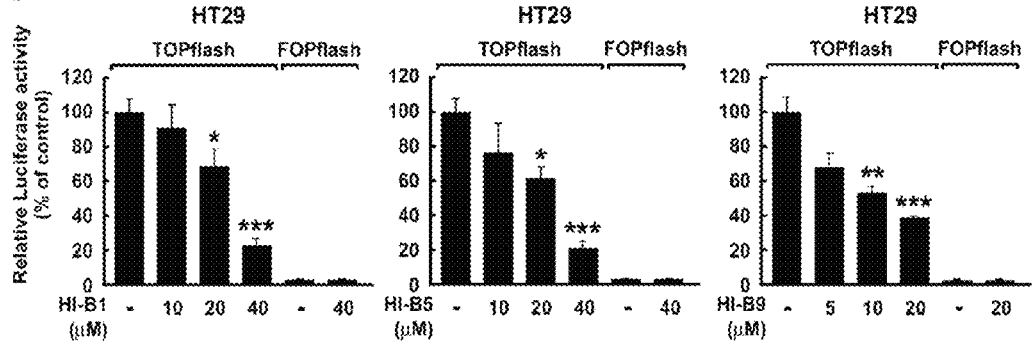

Figure 4
HI-B5 binds to β-catenin but not Tcf-4 to disrupt β-catenin/Tcf-4 complex.
A
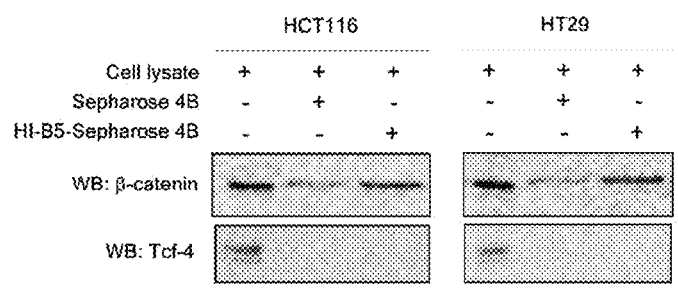
B
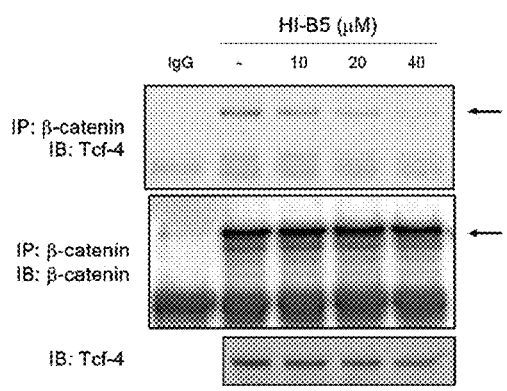
C
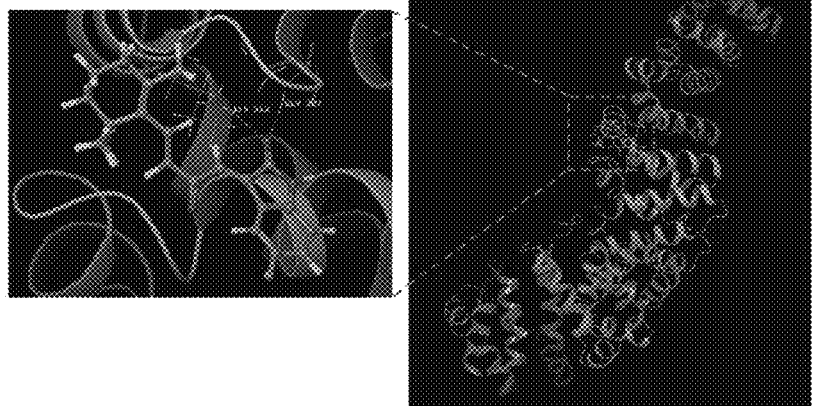

Chemical structures of HI-B12, 13, 16, 17 and 20, derivatives of HI-B9.

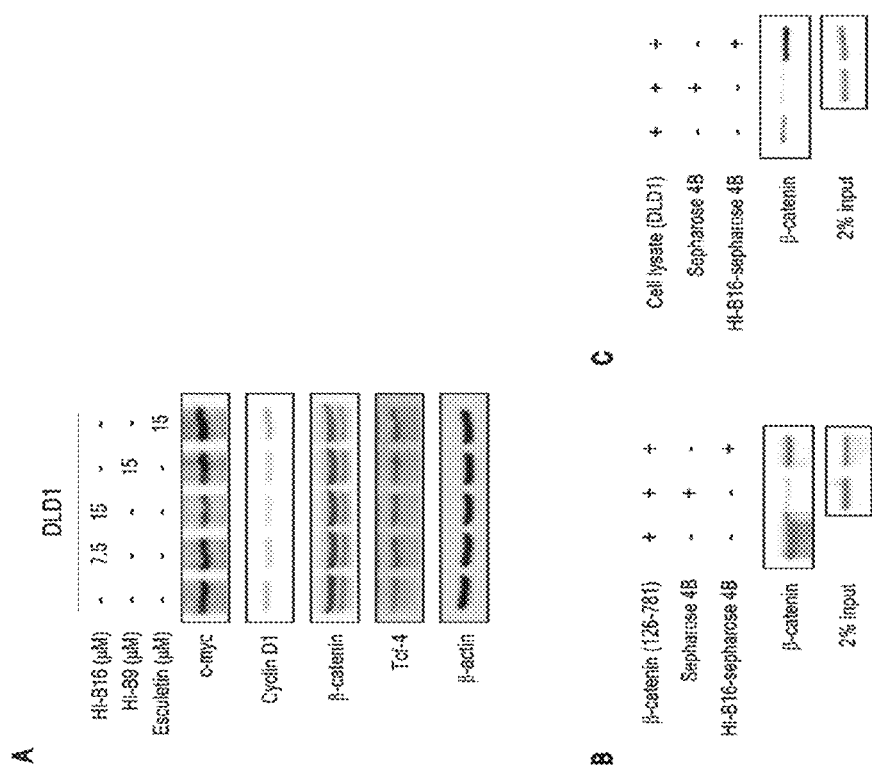

Figure 8A
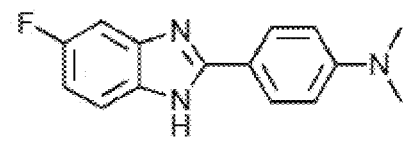
HI-B1 Mol. Weight: 255.296
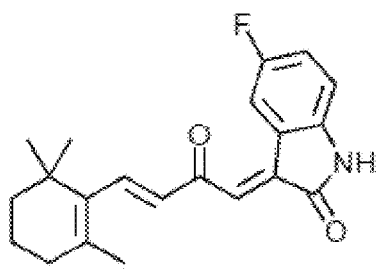
HI-B5 Mol. Weight: 339.410
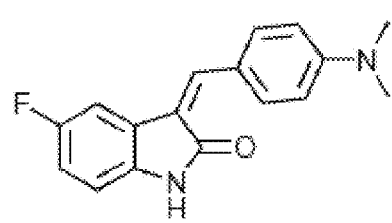
HI-B2 Mol. Weight: 282.318
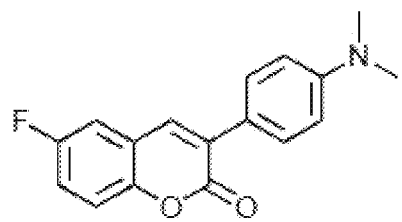
HI-B7 Mol. Weight: 283.302
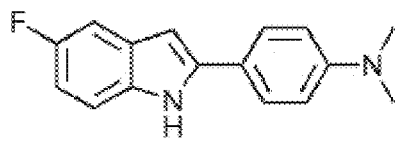
HI-B3 Mol. Weight: 254.308
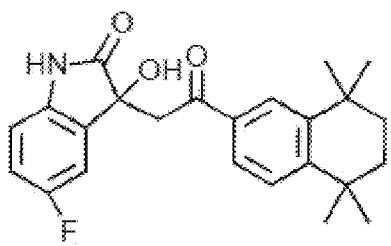
HI-B9 Mol. Weight: 395.474
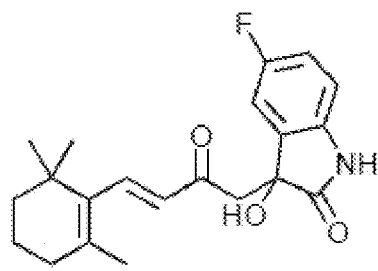
HI-B4 Mol. Weight: 357.425
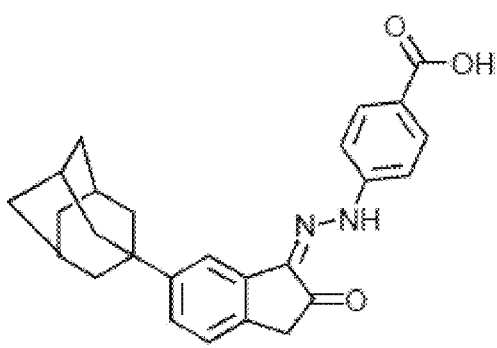
ADA-6 Mol. Weight: 415.493

Figure 8B
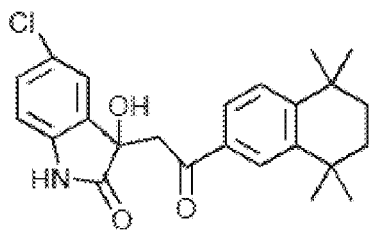
HI-B12 Mol. Weight: 411.9260
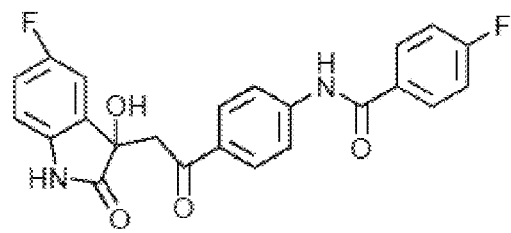
HI-B15 Mol. Weight: 422.3878
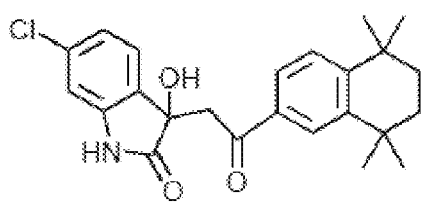
HI-B13 Mol. Weight: 411.9260
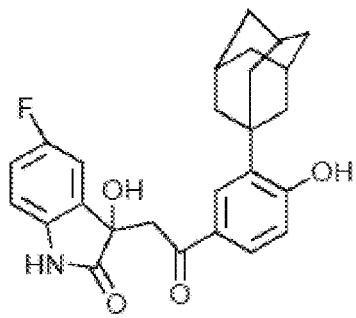
HI-B16 Mol.Weight: 435.4954
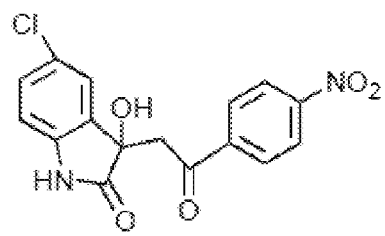
HI-B14 Mol. Weight: 346.7230
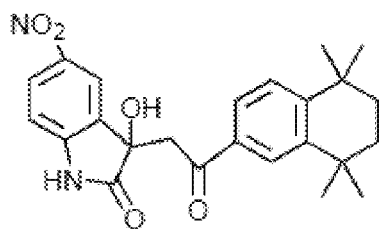
HI-B17 Mol. Weight: 422.4810

Figure 8C
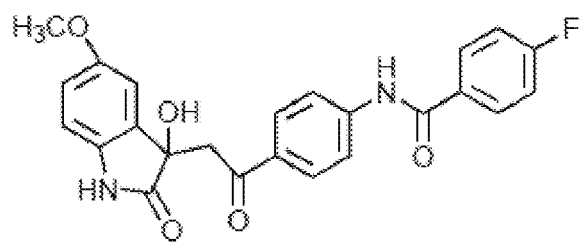
HI-B18 Mol. Weight: 434.4234
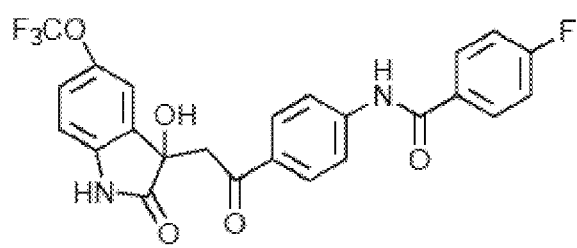
HI-B19 Mol. Weight: 488.3946
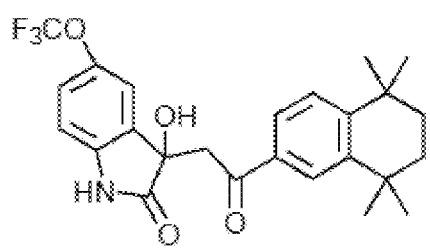
HI-B20 Mol.Weight: 461.4812

INHIBITORS OF BETA-CATENIN IN TREATMENT OF COLORECTAL CANCER

BACKGROUND

Colorectal cancer (CRC) is the third most common cause of cancer death in the USA. Germline mutations in the apc tumor suppressor gene, a key player in CRC development and an important component in the Wnt/β-catenin signaling pathway, are responsible for familial adenomatous polyposis (FAP). Up to 80% of tumors have nuclear accumulation of β-catenin due to inactivating mutations in the gene for adenomatous polyposis *coli* (apc). Mutations that result in constitutive activation of the Wnt/β-catenin signaling pathway can lead to cancer. Wnt(s) have diverse roles in regulating cell fate, proliferation, migration, and death. The APC protein forms a complex with Axin, casein kinase 1 (CK1α, and glycogen synthase kinase 3-β (GSK3-β), which normally phosphorylates β-catenin to target the protein for proteasomal degradation. Mutations or loss of apc in CRC prevent degradation of β-catenin and subsequently lead to constitutive pathway activation. β-catenin binds to the T-cell factor-4 (Tcf-4) in the nucleus and thereby regulates transcription of genes related to growth, development, and differentiation of colonic cryptal cells. Accumulation of cytoplasmic and nuclear β-catenin, which may result from mutations in apc, β-catenin, or axin genes, or from activation of the Wnt signaling pathway, are key in CRC. Since the first report showing that Wnt signaling regulates the stability and translocation of β-catenin the detection of nuclear β-catenin in both laboratory models and in patient tumors has been widely used as a biomarker for demonstrating activation of the Wnt/β-catenin pathway.

Normally, in the absence of Wnt signaling, cytoplasmic β-catenin levels are kept at low levels through a continuous proteasome-mediated degradation by the "destructive complex" comprised of APC, glycogen synthase kinase3-β (GSK3-β), casein kinase 1 (CK1) and Axin. When cells receive Wnt signals, the degradation of β-catenin is suppressed and β-catenin levels build up in the cytoplasm and nucleus. Nuclear β-catenin interacts with the T-cell factor/lymphoid enhancer-binding factor (Tcf/Lef) transcription factor and acts as a transcription regulator for various genes that partially control tumor formation and progression. Once in the nucleus, constitutive activation of β-catenin/Tcf-4 mediates transcription of nuclear target genes.

Familial adenomatous polyposis is an inherited disorder in which patients develop polyps in the colon and rectum. Truncations in APC promote abnormal activation of Wnt/β-catenin signaling and lead to adenomatous lesions and are the most frequent cause of FAP. Mutations in β-catenin and apc are observed in many tumor types, suggesting that deregulation of Wnt/β-catenin signaling is important in the development of cancers. Notably, aberrant Wnt/β-catenin signaling following the loss of APC appears to initiate colon adenoma formation. Nuclear β-catenin was detectable in mouse models exhibiting loss of apc and transgenic mice with stabilized mutant β-catenin developed intestinal adenomas. Overall, studies suggest that deregulation of Wnt/β-catenin is a key oncogenic event that follows the loss of apc.

BRIEF DESCRIPTION OF THE FIGURES

FIGS. 1A-C. HI-B1, HI-B5 and HI-B9 inhibit beta-catenin/Tcf-4 *luciferase* activity in colon cancer cell lines. (A) Chemical structures of three compounds. (B-C) Effects of HI-B1, HI-B5 and HI-B9 on the β-catenin/Tcf-4 *luciferase* activity in HCT116 (B) and HT29 (C) colon cancer cell lines. The compounds suppress transcriptional activity of the β-catenin/Tcf-4 in a dose-dependent manner. Colon cancer cells were co-transfected with reporter genes harboring the β-catenin/Tcf binding site (TOP-flash) or a mutant β-catenin/Tcf binding site (FOP-flash), respectively, and the *Renilla* gene. The *luciferase* activity was normalized to *Renilla* activity.

FIGS. 4A-C. HI-B5 directly binds with β-catenin to disrupt β-catenin/Tcf-4 complex formation. (A) ex vivo binding assay using HCT116 and HT29 cell lysate showed that HI-B5 can interact with β-catenin, but not Tcf-4. (B) Immunoprecipitation assay revealed that binding of HI-B5 to β-catenin caused disruption of β-catenin/Tcf-4 complex in HCT116 cell line. Immunoblot of Tcf-4 after pooling down β-catenin with its antibody showed dose-dependent effect of HI-B5 against β-catenin/Tcf-4 interaction. Tcf-4 expression level was not altered by chemical treatment. (C) Computer docking showed that HI-B5 can form hydrogen bonds at G307 and K312 residues ofβ-catenin.

FIGS. 7A-C. HI-B16 inhibited cyclin D1 and c-myc expression by directly binding with β-catenin in vitro and ex vivo. (A) β-catenin/Tcf-4 activity inhibition resulted in reduction of cyclin D1 and c-myc expression. β-catenin and Tcf-4 expression level were not affected by the small molecule treatment. (B-C) HI-B16 can interact with β-catenin. In vitro binding assay with human β-catenin (126-781 amino acid residues) showed that the purified β-catenin was bound to HI-B16-conjugated sepharose 4B bead (B). Ex vivo binding experiment also resulted in HI-B16/β-catenin binding. 2% of input from each experiments were used to show equal amount of incubated protein (purified or total cell lysates).

FIGS. 8A-C depicts structures of molecules HI-B1 through HI-B20, as disclosed and claimed herein, and which can be suitable for practice of methods of the invention as disclosed and claimed herein.

DETAILED DESCRIPTION

Figure 2:
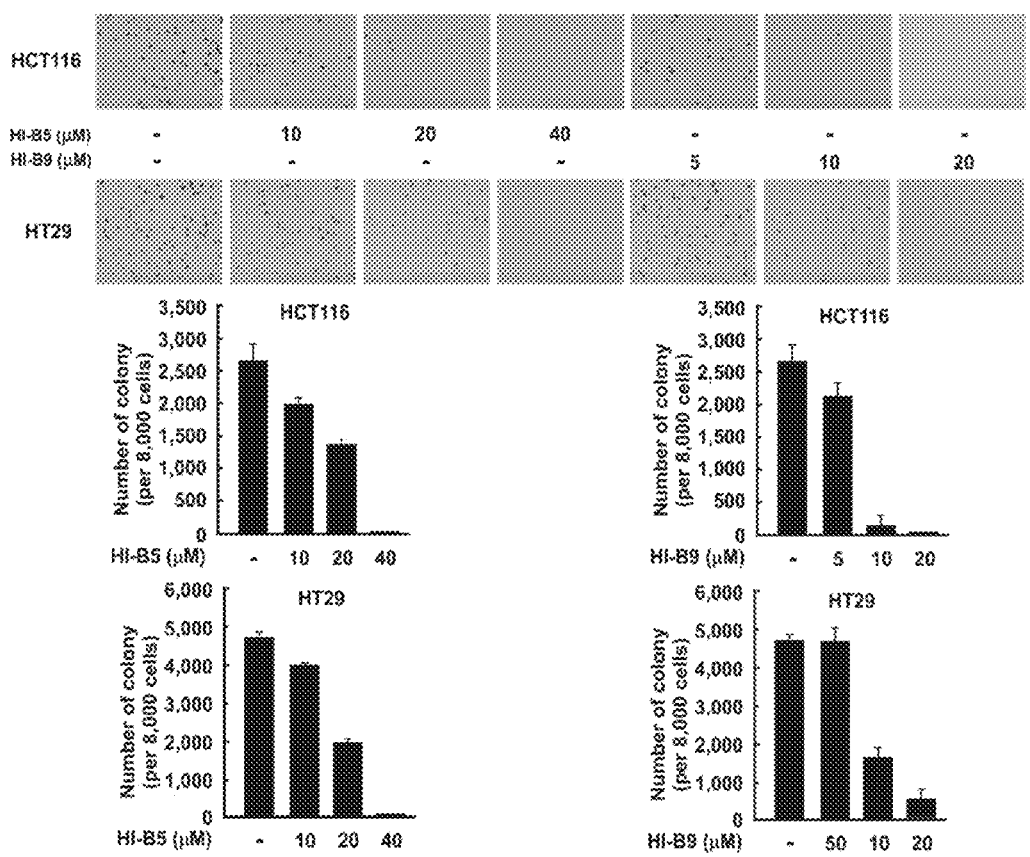
FIG. 2. HI-B5 and HI-B9 suppress anchorage-independent growth of colon cancer cells. HCT116 and HT-29 colon cancer cells. Colony formation of two cell lines were inhibited by treatment of β-catenin inhibitor candidates. Cells ($8\times10^3$/ml) were incubated with or without HI-B5 or HI-B9 compounds in 1 mL of 0.33% BME agar containing 10% FBS or in 3.5 mL of 0.5% BME agar containing 10% FBS. The cultures were maintained at 37° C. in a 5% CO2 incubator for 7 days, after which the cell colonies were counted under a microscope.

Deregulation of canonical Wnt/β-catenin signaling through mutations in apc is now recognized to be an initiating event in CRC and therefore this signaling cascade holds excellent potential as a therapeutic target for treating human cancers. Over the past 20 years, various bioactive compounds ranging from small molecules to targeted antibodies have shown efficacy at suppressing Wnt/β-catenin signaling in experimental settings. Despite academic pursuit and industrial investment, drugs specifically designed to target Wnt/β-catenin signaling have been slow to translate into the clinic, calling for continued effort and novel approaches. A number of inhibitors have been found that act at different steps in the Wnt/β-catenin signal transduction pathway. However, targeting this pathway is complicated because β-catenin has other noncarcinogenic functions such as regulation of cell adhesion through its direct binding with α-catenin and E-cadherin at the membrane surface. Furthermore, in cancers where Wnt signaling is activated by mutations in apc or β-catenin, directly targeting these core components might be a more effective approach than attempting to target upstream events. High-throughput drug screening data indicated that protein—protein interaction sites can also be drug targets. One recent study provided evidence showing that targeting the interaction between β-catenin and Tcf-4 might be an effective method of inhibiting Wnt/β-catenin signaling without adversely affecting the adhesion protein regulatory function of β-catenin.

Using our BlueGene/L and GPU supercomputers, we have identified/synthesized several small molecules that disrupt the β-catenin/Tcf-4 complex resulting in effective attenuation of colon carcinogenesis and are novel potential inhibitors of β-catenin. Our preliminary data showed that two newly identified β-catenin inhibitors, HI-B5 and HI-B9, exert potent anticancer effects on CRC without obvious side effects (see FIG. 1). A natural product, esculetin,

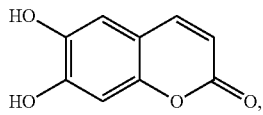

was also found to possess similar bioactivity.

Directly targeting the β-catenin/Tcf-4 complex could be an effective means to prevent or treat colon cancers that exhibit mutations in apc, β-catenin or axin, while avoiding interference with the normal functions of β-catenin. To find potential inhibitors of β-catenin, a molecular docking method using the Glide module from Schrödinger Suite 2011 was used to perform the virtual screening. A crystal structure of a human Tcf-4/β-catenin complex (PDB ID:1JPW) was downloaded from the Protein Data Bank (PDB) for virtual screening studies. The complex is an X-ray diffraction structure with a resolution of 2.5 Å. Waters, metals, and Tcf-4 were stripped from the structure and then hydrogens and atom charges were added to the structures by using the Protein Preparation Wizard in the Schrödinger suite 2011 with the standard procedure outlined therein. Two pockets were generated respectively within a 30-Å 3 grid based on the binding site of Tcf-4 with β-catenin, one is centered with Lys312 and the other is Lys435. A 2D TCMD (Traditional Chinese Medicine Database, Chen, C. Y. (2011) TCM Database@Taiwan: the world's largest traditional Chinese medicine database for drug screening in silico. PloS one, 6, e15939) structure database, which consists of about 20,000 structures of natural products, was first converted to a 3D structure database by using the LigPrep module of the Schrödinger Suite software and then used for virtual screening. High throughput virtual screening (HTVS) docking was first performed because it is intended for the rapid screening of large numbers of ligands followed by standard and extra precision (SP and XP) docking.

We used computational biology technology and medicinal chemistry to identify potential inhibitors of β-catenin. We found that esculetin was predicted to bind to β-catenin at Lys312, Gly307, Lys345, and Asn387 amino acid residues. HI-B5 forms hydrogen bonds at K312, G307 and E396 and HI-B9 forms hydrogen bonds at K312, G307, N430 and R474 of β-catenin. We verified the binding of esculetin, HI-B5 or HI-B9 and β-catenin using esculetin-, HI-B5- or HI-B9-conjugated Sepharose 4B beads and 2-3 different colon cancer cell lines. To further confirm binding, wildtype or mutant β-catenin was transfected into 293T cells and immunoprecipitation and Western blotting were performed. Results indicated that esculetin effectively disrupted the wildtype Tcf-4/β-catenin complex but the mutant Tcf-4/β-catenin complex had no effect. Esculetin also disrupted the nuclear Tcf-4/β-catenin complex in a dose-dependent manner in colon cancer cells. All 3 compounds effectively suppressed proliferation and anchorage-independent growth of colon cancer cells on soft agar. Esculetin, HI-B5 or HI-B9 inhibited transcriptional activity of the β-catenin/Tcf complex in HCT116 colon cancer cells. These compounds effectively inhibited protein expression of Tcf-4/β-catenin targets c-Myc and cyclin D1. Finally, esculetin effectively inhibited xenograft colon cancer tumor growth in nude mice. Tumors were significantly smaller in mice treated with esculetin, which corresponded with decreases in c-Myc and cyclin D1 expression. Overall, esculetin appears to be an effective, non-toxic inhibitor of the Tcf-4/β-catenin complex.

HI-B5 and HI-B9 inhibit beta-catenin/Tcf-4 luciferase activity in colon cancer cell lines, as illustrated in FIG. 1. Compounds HI-B5 and HI-B9 were found to have significant effects on the β-catenin/Tcf-4 luciferase activity in HCT116 (B) and HT29 (C) colon cancer cell lines. HI-B5 and HI-B9 suppress transcriptional activity of the β-catenin/Tcf-4 in a dose-dependent manner. Significant decreases in activity were seen at concentrations of around 10-20 μM concentrations of the two compounds. HI-B5 and HI-B9 were also found to suppress anchorage-independent growth of colon cancer cells in HCT116 and HT-29 colon cancer cells, as evidenced in FIG. 2. Colony formation of the two cell lines were inhibited by treatment of β-catenin inhibitor candidates.

Figure 3:
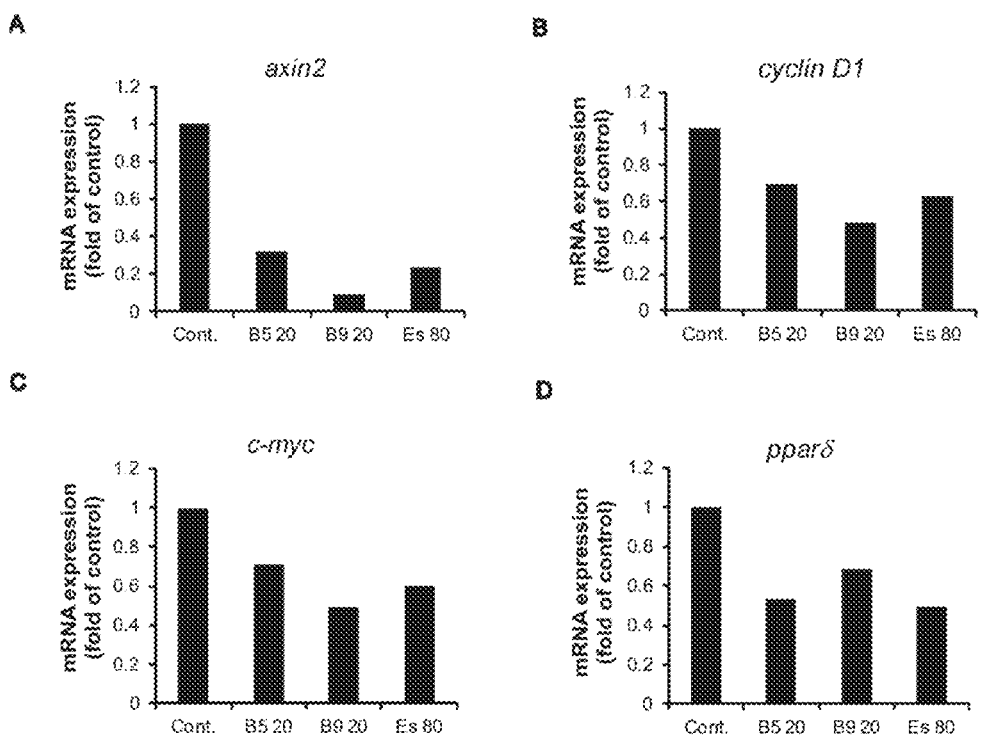
FIGS. 3A-D. HI-B5 and HI-B9 reduce mRNA expression level of target genes expressed by β-catenin/Tcf-4 complex. (A) axin2, (B) cyclin D1, (C) c-myc and (D) pparδ mRNA expression was reduced by HI-B5 40 μM or HI-B9 20 μM treatment. Esculetin was used as a positive control. Expression level of each gene was detected after 12 hr of chemical treatment.

It was further shown, as evidenced in FIG. 3, that HI-B5 and HI-B9 reduce mRNA expression level of target genes expressed by β-catenin/Tcf-4 complex. axin2, cyclin D1, c-myc and pparδ mRNA expression was reduced by HI-B5 40 μM or HI-B9 20 μM treatment. Esculetin was used as a positive control. Expression level of each gene was detected after 12 hr of chemical treatment.

FIG. 4 provides evidence that HI-B5 directly binds with β-catenin to disrupt β-catenin/Tcf-4 complex formation. An ex vivo binding assay using HCT116 and HT29 cell lysate showed that HI-B5 can interact with β-catenin, but not Tcf-4. An immunoprecipitation assay revealed that binding of HI-B5 to β-catenin caused disruption of β-catenin/Tcf-4 complex in HCT116 cell line. Immunoblot of Tcf-4 after pooling down β-catenin with its antibody showed dose-dependent effect of HI-B5 against β-catenin/Tcf-4 interaction. Tcf-4 expression level was not altered by chemical treatment. Computer docking analysis, discussed above, showed that HI-B5 can form hydrogen bonds at G307 and K312 residues of β-catenin.

Figure 5:
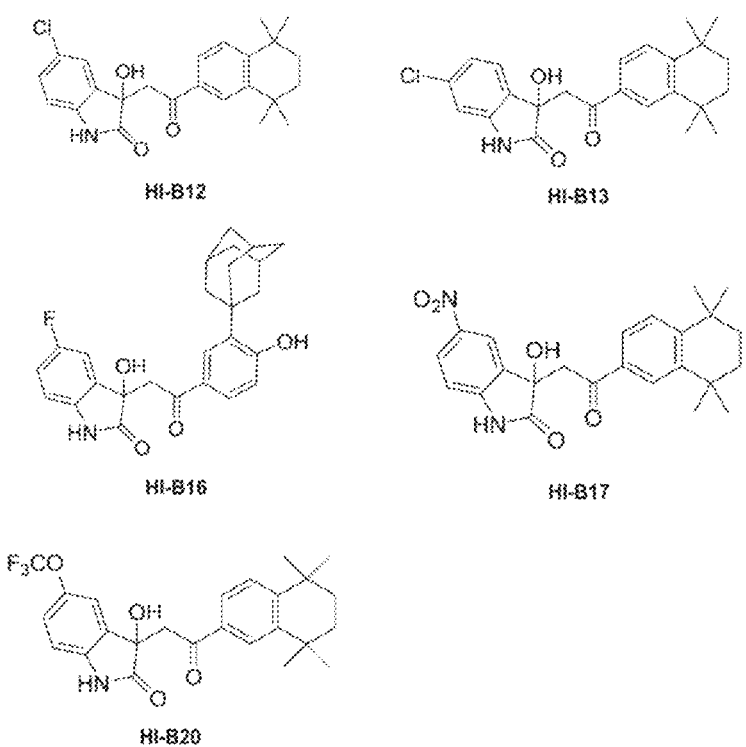
FIG. 5. Chemical structures of HI-B9 derivatives. HI-B12, 13, 16, 17 and 20 were de novo designed and synthesized.
Figure 6:
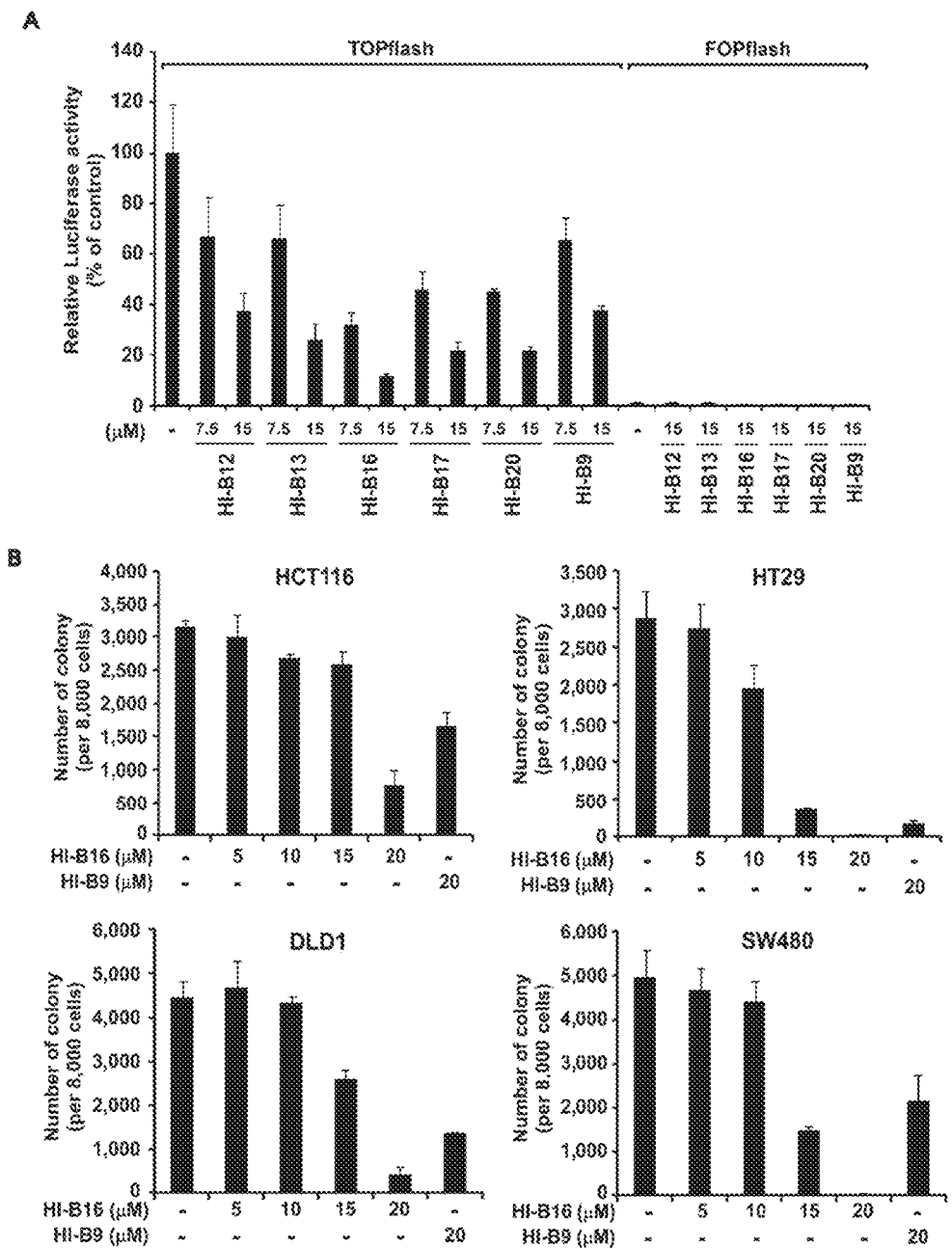
FIGS. 6A-B. HI-B16 shows stronger effect than HI-B9. (A) β-catenin/Tcf-4 *luciferase* assay revealed that HI-B13, 16, 17 and 20s exerted inhibitory effects better than HI-B9, the original chemical of the derivatives. HI-B16 showed ~90% inhibition of *luciferase* activity. (B) HI-B16 inhibited anchorage-independent growth of colon cancer cells. HCT116, HT29, DLD1 and SW480 were incubated in agar plate with or without HI-B16 and HI-B9. In every case, HI-B16 was better than HI-B9 treatment.

Based on the structure of the active compound HI-B9, additional analogs HI-B12, 13, 16, 17 and 20 (FIG. 5) were de novo designed and synthesized. Testing the new compounds, it was found that HI-B 16 shows stronger effect than HI-B9 (FIG. 6). β-catenin/Tcf-4 *luciferase* assay revealed that HI-B13, 16, 17 and 20s exerted inhibitory effects better than HI-B9, HI-B16 showing ~90% inhibition of *luciferase* activity. Compound HI-B16 was also found to inhibit anchorage-independent growth of colon cancer cell lines HCT116, HT29, DLD1 and SW480, which were incubated in agar plate with or without HI-B16 and HI-B9. In every cell line tested, HI-B 16 was more effective than HI-B9 treatment. HI-B 16 inhibited cyclin D1 and c-myc expression by directly binding with β-catenin in vitro and ex vivo. It was shown that β-catenin/Tcf-4 activity inhibition resulted in reduction of cyclin D1 and c-myc expression, and that β-catenin and Tcf-4 expression level were not affected by the small molecule treatment. It was further found that HI-B16 can interact with β-catenin. An in vitro binding assay with human β-catenin (126-781 amino acid residues) showed that the purified β-catenin was bound to HI-B16-conjugated sepharose 4B bead (B). Ex vivo binding experiment also resulted in HI-B16/β-catenin binding. 2% of input from each experiments were used to show equal amount of incubated protein (purified or total cell lysates).

Accordingly, in various embodiments, the invention provides a method of inhibiting β-catenin or disrupting a β-catenin/Tcf-4 complex, comprising contacting the β-catenin with an effective amount or concentration of a compound of formula (I)

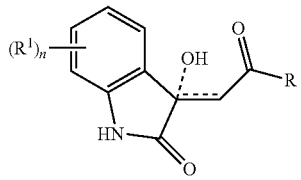
(I)

wherein a dashed line indicates a bond can be present or absent, provided that when the OH group is present on the 2-oxoindole ring, a single bond is present between the 2-oxindole-3-carbon atom and the exocyclic group, and when the OH group is absent, a double bond is present between the 2-oxindole-3-carbon atom and the exocyclic group; R1 is halo and n=0, 1, or 2; R is a cycloalkyl, aryl, or fused aryl-cycloalkyl group, optionally mono- or independently multi-substituted with $(C_1-C_6)$alkyl, $(C_6-C_{12})$cycloalkyl, or hydroxyl; or a pharmaceutically acceptable salt thereof.

Further, the invention provides a method of causing effective attenuation of colon carcinogenesis in a patient, comprising administering to the patient an effective dose of a compound of formula (I)

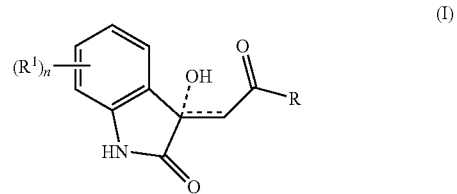
(I)

wherein a dashed line indicates a bond can be present or absent, provided that when the OH group is present on the 2-oxoindole ring, a single bond is present between the 2-oxindole-3-carbon atom and the exocyclic group, and when the OH group is absent, a double bond is present between the 2-oxindole-3-carbon atom and the exocyclic group; R1 is halo and n=0, 1, or 2; R is a cycloalkyl, aryl, or fused aryl-cycloalkyl group, optionally mono- or independently multi-substituted with $(C_1-C_6)$alkyl, $(C_6-C_{12})$cycloalkyl, or hydroxyl; or a pharmaceutically acceptable salt thereof.

For practice of a method of the invention, the compound of formula (I) can be any one of

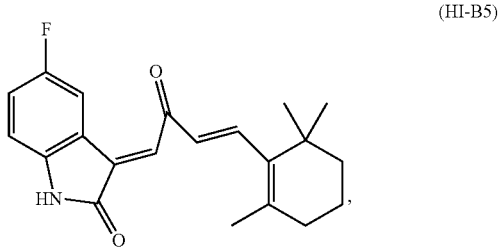
(HI-B5)

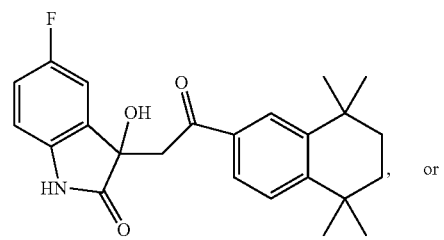
(HI-B9)

, or

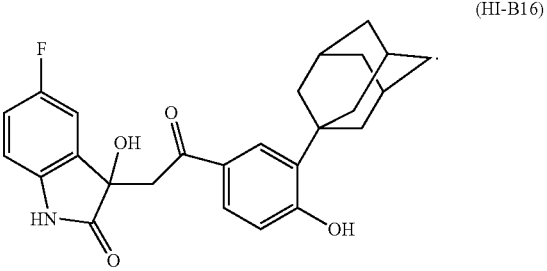
(HI-B16)

In various embodiments, the invention provides a compound of formula (I)

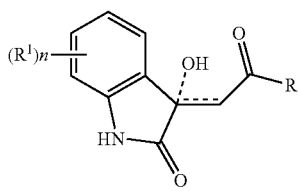
(I)

wherein a dashed line indicates a bond can be present or absent, provided that when the OH group is present on the 2-oxoindole ring, a single bond is present between the 2-oxindole-3-carbon atom and the exocyclic group, and when the OH group is absent, a double bond is present between the 2-oxindole-3-carbon atom and the exocyclic group; $R^1$ is halo and n=0, 1, or 2; R is a cycloalkyl, aryl, or fused aryl-cycloalkyl group, optionally mono- or independently multi-substituted with $(C_1-C_6)$alkyl, $(C_6-C_{12})$cycloalkyl, or hydroxyl; or a pharmaceutically acceptable salt thereof.

For instance, the compound can be any one of

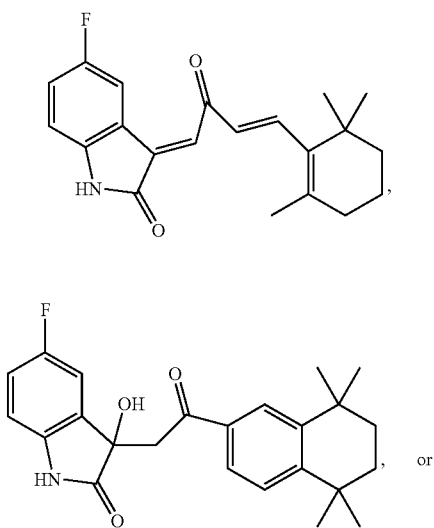

(HI-B5)

(HI-B9)

(HI-B16)

In various embodiments, the invention relates to compounds of the formula (Ia):

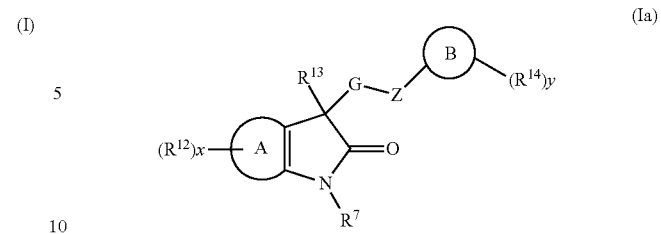

(Ia)

and pharmaceutically acceptable salts thereof;
wherein x is 0, 1, 2, 3 or 4; each $R^{12}$ is independently hydrogen, $(C_1-C_6)$alkyl, $(C_1-C_6)$haloalkyl, $SR^7$ (wherein $R^7$ is hydrogen or $(C_1-C_6)$alkyl), $OR^7$, amino, —O$(C_1-C_6)$alkyl, —$(C_6-C_{12})$aryl or halo; A is $(C_4-C_{12})$heterocyclyl or $(C_6-C_{12})$aryl; $R^{13}$ is hydrogen, $(C_1-C_6)$alkyl, —O$(C_1-C_6)$alkyl, amino, halo or SH; G is $CR^7$, $C(R^7)_2$, O, $NR^7$ or C(O) or $R^{13}$ is absent and G forms a double bond with the carbon atom to which $R^{13}$ would otherwise be attached, and G is $CR^7$; Z is C=$Z^1$, wherein $Z^1$ is O, N—O$(C_1-C_6)$alkyl or N—O—$(C_6-C_{12})$aryl; B is $(C_1-C_6)$alkyl, $(C_6-C_{12})$aryl, $(C_4-C_{12})$heterocyclyl, $(C_6-C_{12})$aryl-$(C_1-C_6)$alkyl or $(C_4-C_{12})$heterocyclyl-$(C_1-C_6)$alkyl; y is 0, 1, 2, 3 or 4; and each $R^{14}$ is independently hydrogen, $(C_1-C_6)$alkyl, $(C_1-C_6)$haloalkyl, $SR^7$, $OR^7$, amino, —O$(C_1-C_6)$alkyl, —$(C_6-C_{12})$aryl or halo. In some embodiments, A forms a phenyl or a pyridyl ring:

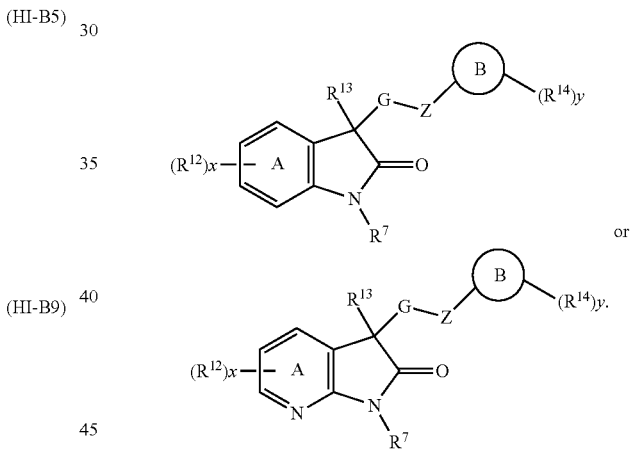

or

In various other embodiments, the invention relates to compounds of the formula (II):

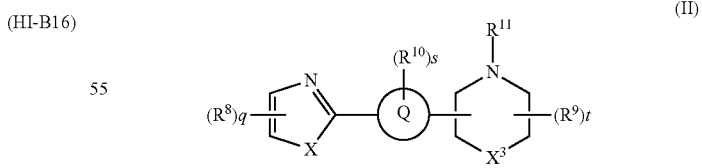

(II)

and pharmaceutically acceptable salts thereof, wherein q is 0, 1 or 2; each $R^8$ is independently hydrogen, $(C_1-C_6)$alkyl, $(C_1-C_6)$haloalkyl, $SR^7$ (wherein $R^7$ is hydrogen or $(C_1-C_6)$alkyl), $OR^7$, amino, —O$(C_1-C_6)$alkyl, —$(C_6-C_{12})$aryl or halo or two adjacent $R^8$ groups, together with the carbon atoms to which they are attached, form a substituted or unsubstitued $(C_6-C_{12})$aryl group or a $(C_4-C_{12})$heterocyclyl group; X is O, S or $NR^7$; Q is $(C_4-C_{12})$heterocyclyl or ($C_6$-$C_{12}$)aryl; s is 0, 1, 2, 3 or 4; each $R^{10}$ is independently hydrogen, $SR^7$, $OR^7$, amino, —O($C_1$-$C_6$)alkyl, —($C_6$-$C_{12}$)aryl or halo; $X^3$ is absent, O, S, C($R^7$)$_2$ or $NR^7$; t is 0, 1, 2, 3, or 4; each $R^9$ is independently hydrogen, $SR^7$, $OR^7$, amino, —O($C_1$-$C_6$)alkyl, —($C_6$-$C_{12}$)aryl or halo; and $R^{11}$ is hydrogen, ($C_1$-$C_6$)alkyl or ($C_6$-$C_{12}$)aryl-($C_1$-$C_6$)alkyl or $R^{11}$ is absent when the nitrogen to which $R^{11}$ would otherwise be attached, is attached to Q; or an $R^{10}$ and an $R^9$ group, together with the atoms to which they are attached, form an substituted or unsubstituted ring; or two adjacent $R^9$ groups, together with the atoms to which they are attached, form a substituted or unsubstitued ($C_6$-$C_{12}$)aryl or a ($C_4$-$C_{12}$)heterocyclyl. In some embodiments the group:

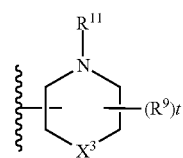

represents

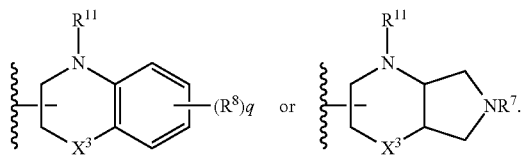

In some embodiments, an $R^{10}$ and an $R^9$ group, together with the atoms to which they are attached, form a ring. One example of such a ring is:

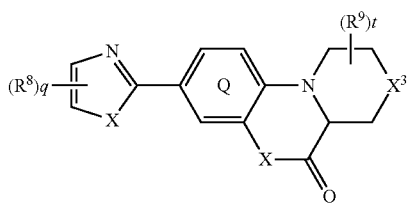

wherein $R^8$, $R^9$, q, t, X, and $X^3$ are as defined herein.

Various embodiments of the present invention also relate to compounds of the formula (III):

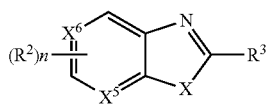

(III)

and pharmaceutically acceptable salts thereof wherein n is 0, 1 or 2; X is O, S or $NR^7$, wherein $R^7$ is hydrogen or ($C_1$-$C_6$)alkyl; $X^5$ and $X^6$ are each, independently, N or CH; each $R^2$ is independently hydrogen, ($C_1$-$C_6$)alkyl, ($C_1$-$C_6$)haloalkyl, $SR^7$, $OR^7$, amino, —O($C_1$-$C_6$)alkyl, —($C_6$-$C_{12}$)aryl or halo; and $R^3$ is ($C_3$-$C_{12}$)cycloalkyl, ($C_6$-$C_{12}$)aryl, ($C_3$-$C_8$)heteroaryl or fused ($C_6$-$C_{12}$)aryl-($C_5$-$C_{12}$)cycloalkyl, optionally mono- or independently multi-substituted, in some embodiments, with ($C_1$-$C_6$)alkyl, ($C_3$-$C_{12}$)cycloalkyl, or hydroxyl.

In some embodiments, $R^3$ is ($C_6$-$C_{12}$)aryl. In other embodiments, $R^3$ is phenyl, pyridyl, furanyl or thiophenyl, such that the invention relates to compounds of the formula (IV) and (IVa):

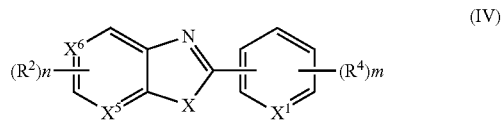

(IV)

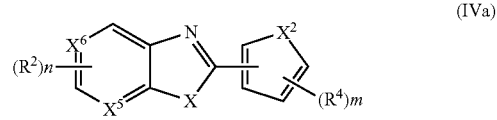

(IVa)

and pharmaceutically acceptable salts thereof, wherein $R^2$, X, $X^5$, $X^6$, and n are as defined above; m is 0, 1 or 2; each $R^4$ is independently hydrogen, $SR^7$, $OR^7$, amino, —O($C_1$-$C_6$)alkyl, —($C_6$-$C_{12}$)aryl or halo; $X^1$ is N or CH; $X^2$ is O, NH or S.

In various other embodiments, the invention relates to compounds of the formulae (V), (Va), (VI), and (VIa):

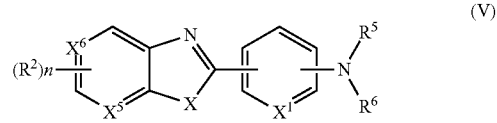

(V)

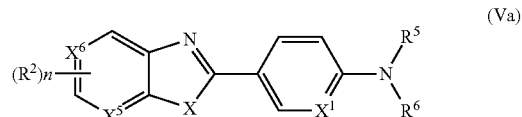

(Va)

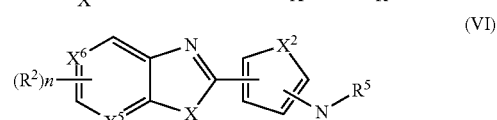

(VI)

(VIa)

and pharmaceutically acceptable salts thereof, wherein $R^2$, X, $X^1$, $X^2$, $X^5$, $X^6$, and n are as defined above; and $R^5$ and $R^6$ are each, independently, ($C_1$-$C_6$)alkyl, ($C_3$-$C_{12}$)cycloalkyl, ($C_6$-$C_{12}$)aryl or, $R^5$ and $R^6$, together with the nitrogen to which they are attached, form a ($C_4$-$C_{12}$)heterocyclyl group which, in turn, is optionally substituted.

Various embodiments of the present invention also relate to compounds of the formulae (VII)-(XII):

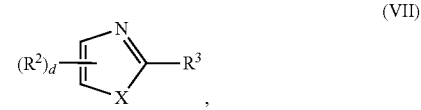

(VII)

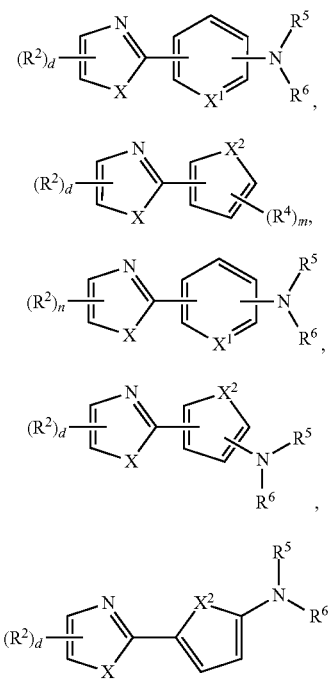

and pharmaceutically acceptable salts thereof, wherein $R^2$, $R^3$, $R^5$, $R^6$, X, $X^1$, $X^2$, and m are as defined above; and d is 0, 1 or 2.

In some embodiments, X in the compound of the formulae (II), (III), (IV), (IVa), (V), (Va), and (VI)-(XII) is $NR^7$. In some embodiments, $R^7$ is hydrogen.

In other embodiments, n in the compound of the formulae (II), (III), (IV), (IVa), (V), (Va), and (VI)-(XII) is 1 or 2 and $R^2$ is halo or $(C_1$-$C_6)$trihaloalkyl.

Specific compounds that fall under one or more of the formulae (II), (III), (IV), (IVa), (V), (Va), and (VI)-(XII) include the following compounds:

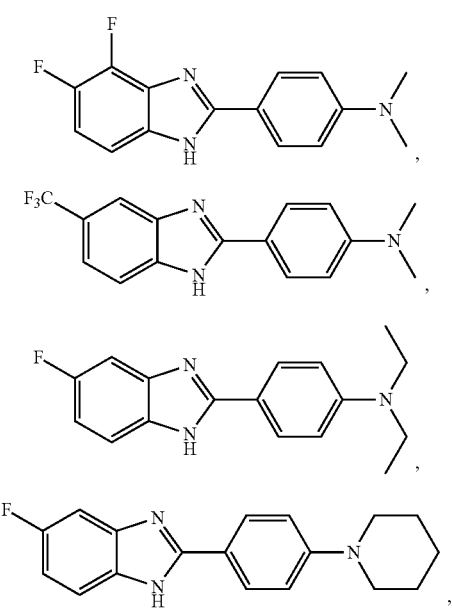

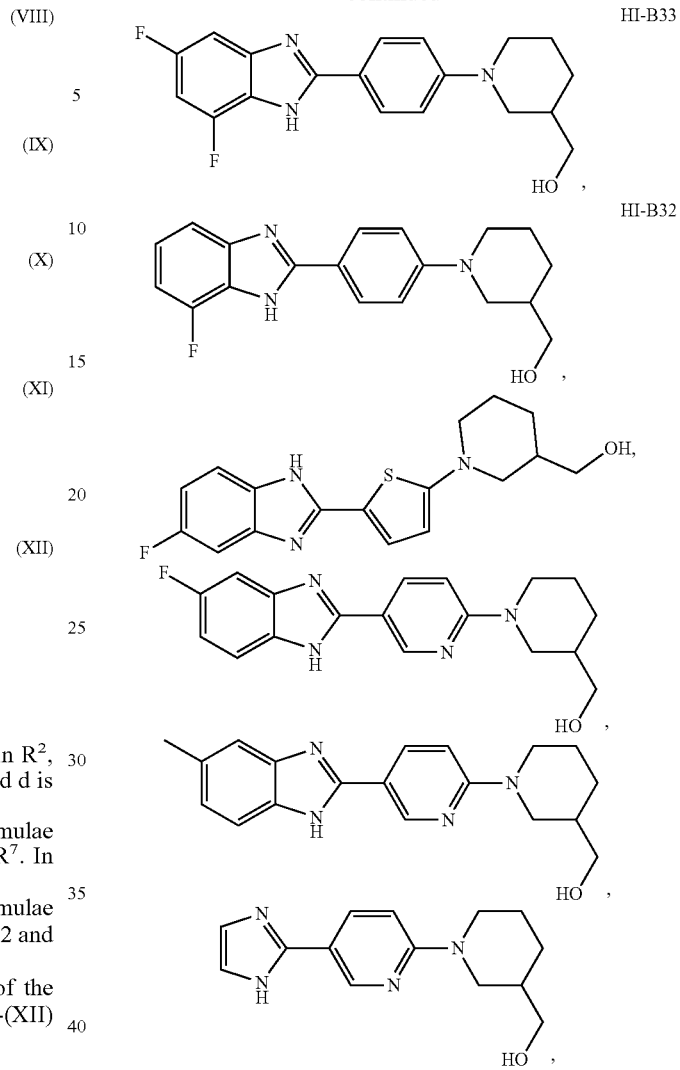

and pharmaceutically acceptable salts thereof.

In various embodiments, the invention provides a method of inhibiting β-catenin or disrupting a β-catenin/Tcf-4 complex, comprising contacting the β-catenin with an effective amount or concentration of a compound of formulae (I)-(IVa) or a pharmaceutically acceptable salt thereof.

In various other embodiments, the invention provides a method of causing effective attenuation of colon carcinogenesis in a patient, comprising administering to the patient an effective dose of a compound of formulae (II)-(IVa).

In some embodiments, the compounds described herein, which fall under the formulae (I)-(IVa) have an $IC_{50}$ of from about 2 μM to about 50 μM.

In some embodiments, the compounds of the formulae (I), (Ia), (II), (III), (IIIa), (IV), (Iva), (V), (Va), and (VI)-(XII) are β-catenin-selective inhibitors. One indication that a compound is a β-catenin-selective inhibitor is that it suppresses β-catenin-dependent cell lines (e.g., DLD1, HCT116, and HT29), but not β-catenin-independent cell lines (e.g., H838). In some embodiments, compounds are β-catenin-selective inhibitor when the compound's $IC_{50}$ against β-catenin-dependent cell lines is 10-25 times lower than the $IC_{50}$ against β-catenin-independent cell lines. Thus, for example, if a given compound has an $IC_{50}$ against a β-catenin-dependent cell line of from about 2 μM to about 50 μM and the compound is a β-catenin-selective inhibitor, it would be expected to have an $IC_{50}$ against a β-catenin-independent cell line of from about 50 μM to about 500 μM.

The terms "halo," "halogen," or "halide" group, as used herein, by themselves or as part of another substituent, mean, unless otherwise stated, a fluorine, chlorine, bromine, or iodine atom.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to 12 ring members, whereas in other embodiments the number of ring carbon atoms range from 3 to 4, 5, 6, or 7. In some embodiments, cycloalkyl groups can have 5 to 12 carbon atoms ($C_5$-$C_{12}$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 12 carbons ($C_6$-$C_{12}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2- or 3-substituted phenyl or 2-5 substituted naphthyl groups, which can be substituted with groups such as those described herein.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "fused arylcycloalkyl" as used herein refers to substituted or unsubstituted groups where an aryl group, as defined herein, is fused to a cycloalkyl group, as that group is defined herein. Non-limiting examples of fused arylcycloalkyl groups include groups having the formula:

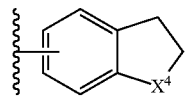

wherein $X^4$ represents $(-CH_2-)_p$, wherein p is 0, 1, 2, or 3.

The term "haloalkyl" group, as used herein, includes mono-halo alkyl groups, poly-halo alkyl groups, including trihaloalkyl groups, wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "amino" as used herein refers to a substituent of the form $-NR_2$, $-NR_3^+$, wherein each R is independently selected from hydrogen, alkyl, aryl, and arylalkyl. In some embodiments, two R groups attached to the nitrogen atom, together with the nitrogen atom to which the R groups are attached, can form a heterocyclyl group, as that term is defined herein. Accordingly, any compound substituted with an amino group can be viewed as an amine.

The term "heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl or a heteroaryl, or if polycyclic, any combination thereof. In some embodiments, heterocyclyl groups include 3 to about 20 ring members, whereas other such groups have 3 to about 15 or 4 to about 12 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$). A heterocyclyl group designated as a $C_2$-heterocyclyl can be a 5-membered ring with two carbon atoms and three heteroatoms, a 6-membered ring with two carbon atoms and four heteroatoms and so forth. In sum, the number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups. Examples of indolinonyl, isoindolinyl, benzoxazolinyl, and benzthiazolinyl groups include groups having the formulae:

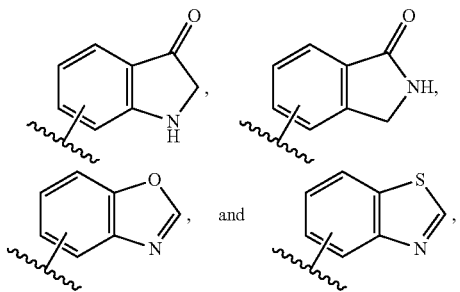

respectively, each of which may be substituted or unsubstituted.

The term "substituted" as used herein refers to a molecule in which one or more hydrogen atoms contained therein are replaced by one or more non-hydrogen atoms or substituents. Examples of substituents include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents, J, that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR, SOR, SO$_2$R', SO$_2$N(R')$_2$, SO$_3$R', (CH$_2$)$_{0-2}$P(O)OR'$_2$, C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')C(O)OR', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R)SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, arylalkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

EXAMPLES

The following examples are included to demonstrate specific embodiments of the invention. However, many changes can be made in the specific embodiments which are disclosed and still obtain a like or similar result without departing from the spirit and scope of the invention.

Example 1

Materials and Methods
Synthesis

Compounds such as HI-B5 and HI-B9, used in practice of methods of the invention, can be prepared according to Synthetic Scheme 1, using condensation of appropriately substituted isatins and methyl ketones in the initial aldol condensation, optionally followed by dehydration:

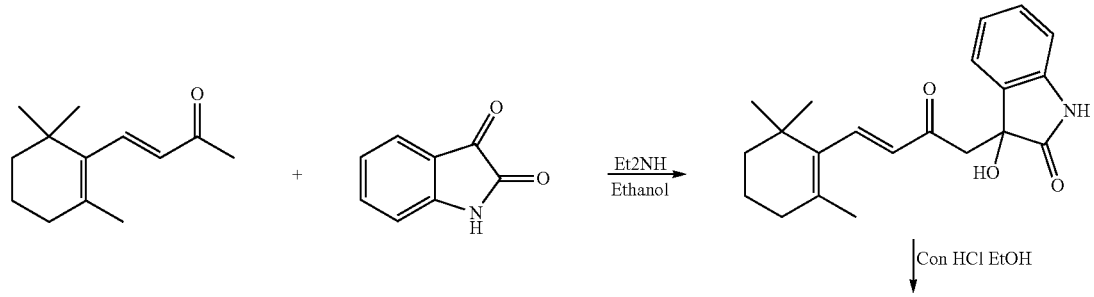

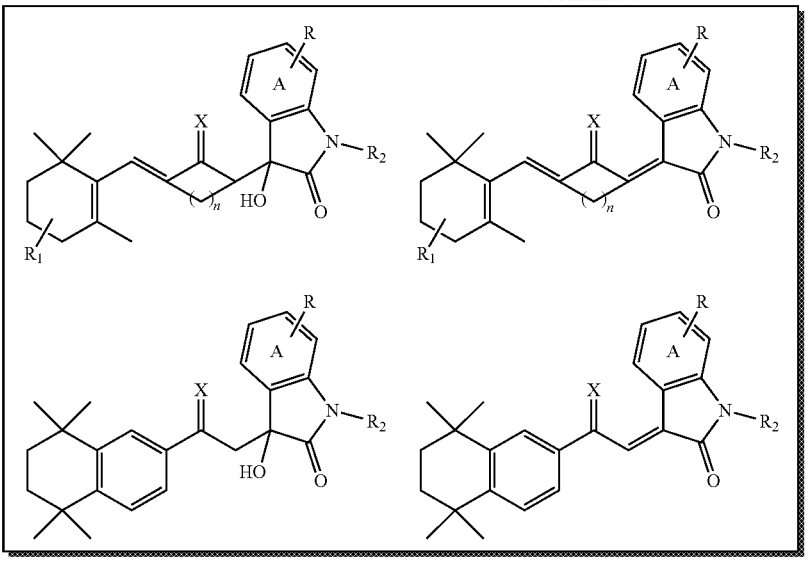

Compound HI-B16 can be prepared by an analogous route using a 3-adamantyl-4-hydroxybenzophenone reagent in the condensation reaction with isatin (1H-indole-2,3-dione). Selection of an isatin precursor and a methyl ketone precursor bearing the desired substituent pattern is within ordinary skill, and they can either be purchased from a commercial supplier or prepared using ordinary knowledge and skill in the art. For instance, compounds HI-B5, HI-B9, and HI-B16 can all be prepared from 5-fluoroisatin, which can be purchased from Sigma-Aldrich and other suppliers. Methyl ketone precursors can be purchased or synthesized using ordinary knowledge and skill, and the two precursors condensed under aldol conditions, optionally followed by dehydration using any of the methods well-known in the art.

Synthetic Procedures:

Synthesis of HI-B5

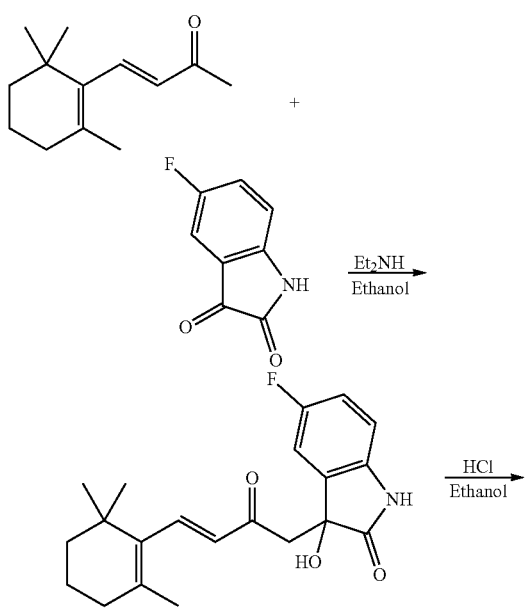

-continued

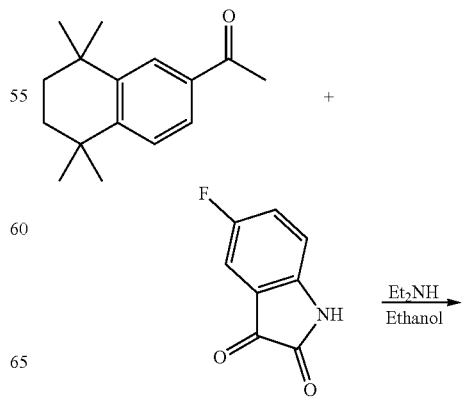

HI-B5

To a stirred solution of 5-fluoroisatin (10 mmol) and diethylamine (0.3 mmol) in ethanol was added β-ionone (10 mmol). The resulting mixture was stirred at room temperature for 72 h. After this time, the solution was evaporated and purified by column chromatography to give 3-hydroxy intermediate.

To a stirred solution of the above 3-hydroxy intermediate (0.25 g) in ethanol (5 mL) was added 37% HCl (1.0 mL). The resulting reaction mixture was stirred at room temperature. After 4 h, the red solution was diluted with water and the precipitated red solid was filtered and purified by recrystallization from ethanol.

Synthesis of HI-B9

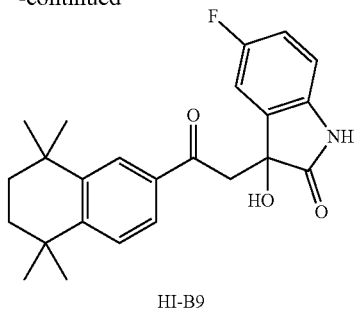

HI-B9

To a stirred solution of 5-fluoroisatin (10 mmol) and diethylamine (0.3 mmol) in ethanol was added 1-(5,5,8,8-Tetramethyl-5,6,7,8-tetrahydronaphthalen-2-yl)ethanone (10 mmol). The resulting mixture was stirred at room temperature for 72 h. After this time, the solution was evaporated and purified by recrystallization (ethyl acetate/n-hexane).

Synthesis of HI-B 16

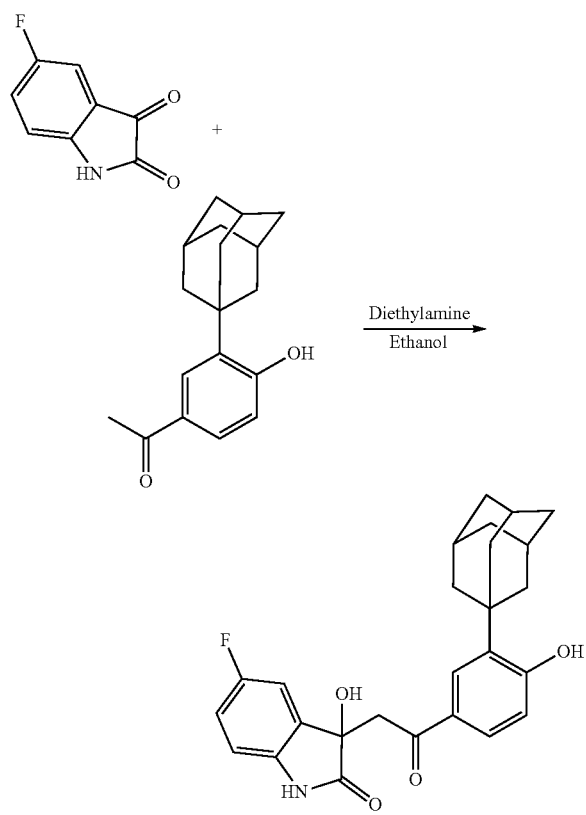

To a stirred solution of 5-fluoroisatin (10 mmol) and diethylamine (0.3 mmol) in ethanol was added 3-(1-Adamantyl)-4-hydroxyacetophenone (10 mmol). The resulting mixture was stirred at room temperature for 7 days. After this time, the solution was evaporated and purified by recrystallization (ethyl acetate/n-hexane).

Example 2

Colon Cancer Cell Lines.

Various cell lines with APC/β-catenin mutations were used as shown below (Table 1).

TABLE 1

Mutations of APC and β-catenin in various colon cancer cell lines

| Cell lines | APC | β-catenin | Reference |
|---|---|---|---|
| HCT116 | WT | WT/mutant (exon 3) | (1) |
| DLD1 | mutant | WT | (2) |
| SW480 | mutant | WT | (3) |
| HT29 | mutant | WT | (4) |

Luciferase Reporter Assay.

Transient transfection was performed using jetPEI and assays to detect firefly luciferase and *Renilla* activities according to the manufacturer's manual (Promega). Briefly, cells were seeded onto 10-cm plates and co-transfected with 400 ng of the *Renilla luciferase* internal control gene and 4 μg of the TOP-flash luciferase reporter construct containing three tandem Tcf consensus binding sites upstream of luciferase cDNA, or the FOPflash luciferase reporter construct, a plasmid with mutated Tcf binding sites. After 16 h of transfection, cells were trypsinized and seeded onto 48-well plates, and cells were treated with respective chemicals for 24 h. Luciferase and Renilla activities were measured using their substrates.

Soft Agar Assay.

Cells ($8 \times 10^3$ per well) suspended in Basal Medium Eagle (BME) supplemented with 10% FBS were added to 0.3% agar with different doses of chemicals in a top layer over a basal layer of 0.6% agar. The cultures were maintained at 37° C. in a 5% $CO_2$ incubator for 2 wk and then colonies were counted under a microscope using the Image-Pro Plus Software (v.4) program (Media Cybernetics).

Virtual Docking.

The Glide module from Schrödinger Suite 2011 was used for virtual screening. A crystal structure of a human β-catenin structure (PDB ID:1JPW) was downloaded from the Protein Data Bank for virtual screening studies. The binding pocket was selected around the K312 and K435 residues, which are reported to be important in the β-catenin/Tcf-4 binding mode. The docking was performed more than 30 times, and the most frequent outcomes of β-catenin in chemical-protein interaction was selected as possible binding residues.

Pull-Down Assay.

Protein extracts (500 μg) of colon cancer cells were mixed with Sepharose-4B beads (as a negative control) or chemical-conjugated Sepharose 4B beads (100 μl) in reaction buffer. After being washed five times with buffer, the proteins were visualized by Western blot analysis.

Immunoprecipitation Assay.

Colon cancer cells treated or not treated with low or high concentrations of compounds for 24 h were disrupted with lysis buffer (50 mmol/L Tris, pH 8, 250 mmol/L NaCl, 5 mmol/L EDTA, 0.1% NP-40, 10% glycerol, and 1× protease inhibitor cocktail). Cell lysates were cleared by centrifugation, and immunoprecipitations were performed by incubating overnight with anti-β-catenin. Agarose beads were then added and samples incubated for 3 h at 4° C. After removing unbound proteins by washing five times with lysis buffer, bound proteins were harvested by boiling in sample buffer, and resolved by 8% SDS-PAGE. β-Catenin and Tcf-4 proteins were visualized using a chemiluminescence reagent (Amersham).

Western Blot Analysis.

Proteins from cell lysates were prepared, separated by SDS-PAGE and transferred to Immobilon-P membranes (Millipore Corporation, Billerica, Mass.). Membranes were blocked with 5% nonfat dry milk for 1 h at room temperature and incubated with each of the primary and secondary antibodies. The signal was detected with a chemiluminescence reagent (Amersham).

RNA Isolation and Quantitative Real-Time PCR.

RNA isolation was performed according to the Trizol reagent protocol (catalog #15596-018, Invitrogen). The concentration and the purity of RNA was determined by measuring the absorbance at 260/280 nm. cDNA was synthesized using 1 µg of RNA and the amfiRevert Platinum cDNA synthesis master mix (GenDEPOT, Cat. No. R5600). For real time PCR, 1 µl of the synthesized cDNA was loaded into 1 well of a 96-well plate for detection of specific target genes using the Power SYBR Green PCR master mix (ABsystems, #4367659).

DOCUMENTS CITED

1. Ilyas M, Tomlinson I P, Rowan A, Pignatelli M, Bodmer W F. Beta-catenin mutations in cell lines established from human colorectal cancers. Proc Natl Acad Sci U S A. 1997; 94:10330-4.
2. Cong F, Zhang J, Pao W, Zhou P, Varmus H. A protein knockdown strategy to study the function of beta-catenin in tumorigenesis. BMC Mol Biol. 2003; 4:10.
3. Sadot E, Geiger B, Oren M, Ben-Ze'ev A. Down-regulation of beta-catenin by activated p53. Mol Cell Biol. 2001; 21:6768-81.
4. Lepourcelet M, Chen Y N, France D S, Wang H, Crews P, Petersen F, et al. Small-molecule antagonists of the oncogenic Tcf/beta-catenin protein complex. Cancer Cell. 2004; 5:91-102.

What is claimed is:

1. A method of inhibiting β-catenin or disrupting a β-catenin/Tcf-4 complex, comprising contacting the β-catenin with an effective amount or concentration of a compound of formula (II):

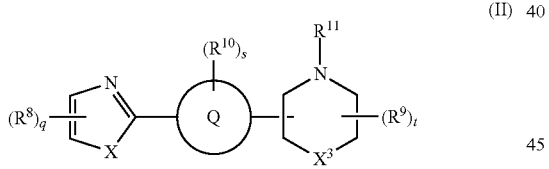

and pharmaceutically acceptable salts thereof, wherein:
q is 2, two adjacent $R^8$ groups, together with the carbon atoms to which they are attached, form a substituted or unsubstitued $(C_6\text{-}C_{12})$aryl group or a $(C_4\text{-}C_{12})$ heterocyclyl group, and Q is $(C_4\text{-}C_{12})$heterocyclyl or $(C_6\text{-}C_{12})$aryl;
q is 1, $R^8$ is independently hydrogen, $(C_1\text{-}C_6)$alkyl, $(C_1\text{-}C_6)$haloalkyl, $SR^7$ (wherein $R^7$ is hydrogen or $(C_1\text{-}C_6)$alkyl), $OR^7$, amino, —O$(C_1\text{-}C_6)$alkyl, —$(C_6\text{-}C_{12})$aryl or halo, and Q is $(C_4\text{-}C_{12})$heterocyclyl or $(C_6\text{-}C_{12})$aryl; or
q is 0 and Q is a pyrydinyl group;
X is O, S or $NR^7$;
s is 0, 1, 2, 3 or 4;
each $R^{10}$ is independently hydrogen, $SR^7$, $OR^7$, amino, —O$(C_1\text{-}C_6)$alkyl, —$(C_6\text{-}C_{12})$aryl or halo; $X^3$ is absent, O, S, $C(R^7)_2$ or $NR^7$;
t is 0, 1, 2, 3, or 4;
each $R^9$ is independently hydrogen, $SR^7$, $OR^7$, amino, —O$(C_1\text{-}C_6)$alkyl, —$(C_6\text{-}C_{12})$aryl or halo; and $R^{11}$ is hydrogen, $(C_1\text{-}C_6)$alkyl or $(C_6\text{-}C_{12})$aryl-$(C_1\text{-}C_6)$alkyl; or
$R^{11}$ is absent when the nitrogen to which $R^{11}$ would otherwise be attached, is attached to Q; or
an $R^{10}$ and an $R^9$ group, together with the atoms to which they are attached, form an substituted or unsubstituted ring; or
two adjacent $R^9$ groups, together with the atoms to which they are attached, form a substituted or unsubstitued $(C_6\text{-}C_{12})$aryl or a $(C_4\text{-}C_{12})$heterocyclyl.

2. A method of inhibiting β-catenin or disrupting a β-catenin/Tcf-4 complex, comprising contacting the β-catenin with an effective amount or concentration of a compound of formula (III):

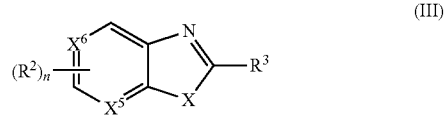

and pharmaceutically acceptable salts thereof, wherein:
n is 0, 1 or 2;
each $R^2$ is independently hydrogen, $(C_1\text{-}C_6)$alkyl, $(C_1\text{-}C_6)$haloalkyl, $SR^7$, $OR^7$, amino, —O$(C_1\text{-}C_6)$alkyl, —$(C_6\text{-}C_{12})$aryl or halo X is O, S or $NR^7$, wherein $R^7$ is hydrogen or $(C_1\text{-}C_6)$alkyl;
$X^5$ and $X^6$ are each, independently, N or CH; and
$R^3$ is $(C_3\text{-}C_{12})$cycloalkyl, $(C_6\text{-}C_{12})$aryl, $(C_3\text{-}C_8)$heteroaryl or fused $(C_6\text{-}C_{12})$aryl-$(C_5\text{-}C_{12})$cycloalkyl.

3. The method of claim 2, wherein the compound of the formula (II) is a compound of the formula (V) or (VI):

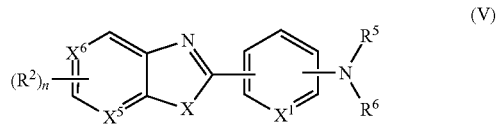

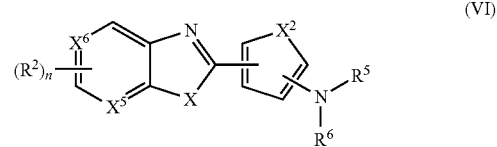

and pharmaceutically acceptable salts thereof, wherein:
$X^1$ is N or CH;
$X^2$ is O, NH or S; and
$R^5$ and $R^6$ are each, independently, $(C_1\text{-}C_6)$alkyl, $(C_3\text{-}C_{12})$cycloalkyl, $(C_6\text{-}C_{12})$aryl or, $R^5$ and $R^6$, together with the nitrogen to which they are attached, form a $(C_4\text{-}C_{12})$heterocyclyl group which, in turn, is optionally substituted.

4. A method of inhibiting β-catenin or disrupting a β-catenin/Tcf-4 complex, comprising contacting the β-catenin with an effective amount or concentration of a compound of formula (VII), (VIII), (IX), (X), (XI) or (XII):

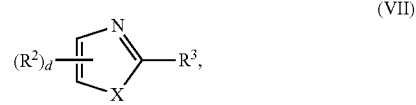

-continued

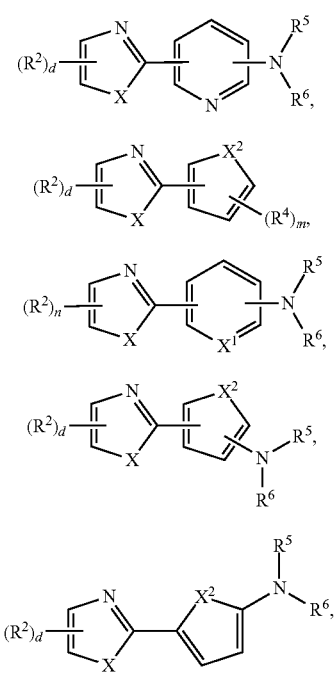

and pharmaceutically acceptable salts thereof, wherein:
d is 0, 1 or 2;
m is 0, 1 or 2;
each $R^2$ is independently hydrogen, $(C_1-C_6)$alkyl, $(C_1-C_6)$haloalkyl, $SR^7, OR^7$, amino, —O$(C_1-C_6)$alkyl, —$(C_6-C_{12})$aryl or halo;
$X^1$ is N or CH;
$X^2$ is O, NH or S;
$R^3$ is $(C_3-C_{12})$cycloalkyl, $(C_6-C_{12})$aryl, $(C_3-C_8)$heteroaryl or fused $(C_6-C_{12})$aryl-$(C_5-C_{12})$cycloalkyl;
each $R^4$ is independently hydrogen, $SR^7$, $OR^7$, amino, —O$(C_1-C_6)$alkyl, —$(C_6-C_{12})$aryl or halo;
$R^5$ and $R^6$ are each, independently, $(C_1-C_6)$alkyl, $(C_3-C_{12})$cycloalkyl, $(C_6-C_{12})$aryl or, $R^5$ and $R^6$, together with the nitrogen to which they are attached, form a $(C_4-C_{12})$heterocyclyl group which, in turn, is optionally substituted; and
$R^7$ is hydrogen or $(C_1-C_6)$alkyl.

5. A method of inhibiting β-catenin or disrupting a β-catenin/Tcf-4 complex, comprising contacting the β-catenin with an effective amount or concentration of a compound of formula:

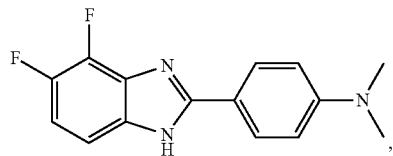

HI-B22

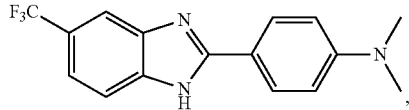

HI-B23

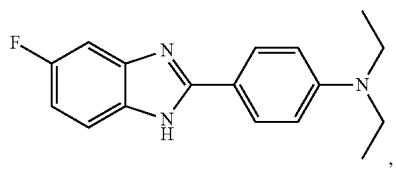

HI-B24

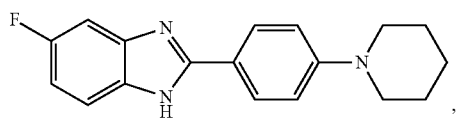

HI-B26

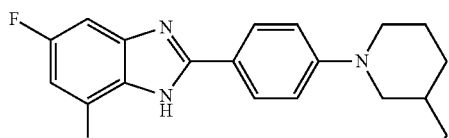

HI-B33

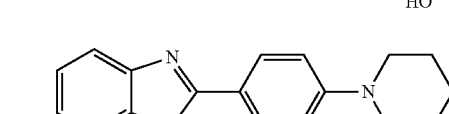

HI-B32

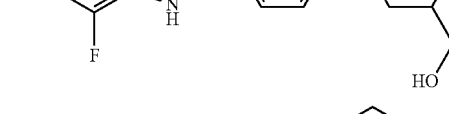

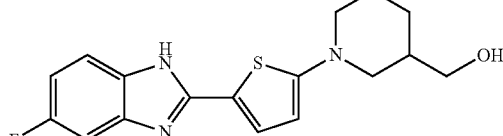

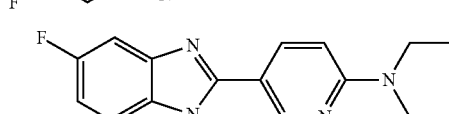

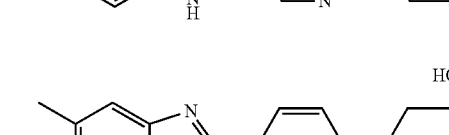

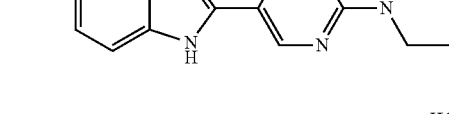

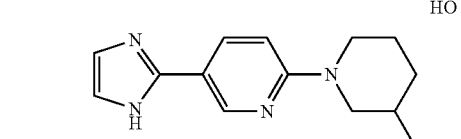

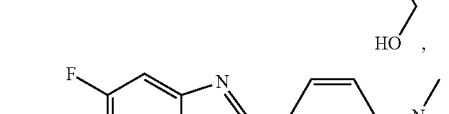

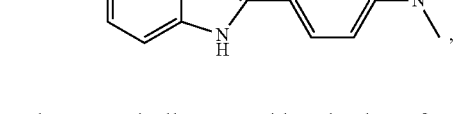

or pharmaceutically acceptable salts thereof.

6. A method of causing effective attenuation of colon carcinogenesis in a patient, comprising administering to the patient an effective dose of a compound of formula (II):

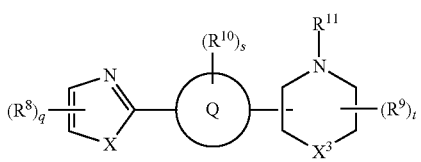

(II)

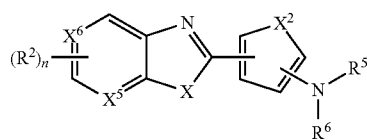

(VI)

and pharmaceutically acceptable salts thereof, wherein:
q is 2, two adjacent $R^8$ groups, together with the carbon atoms to which they are attached, form a substituted or unsubstitued $(C_6-C_{12})$aryl group or a $(C_4-C_{12})$ heterocyclyl group, and Q is $(C_4-C_{12})$heterocyclyl or $(C_6-C_{12})$aryl;
q is 1, $R^8$ is independently hydrogen, $(C_1-C_6)$alkyl, $(C_1-C_6)$haloalkyl, $SR^7$ (wherein $R^7$ is hydrogen or $(C_1-C_6)$alkyl), $OR^7$, amino, —O$(C_1-C_6)$alkyl, —$(C_6-C_{12})$aryl or halo, and Q is $(C_4-C_{12})$heterocyclyl or $(C_6-C_{12})$aryl; or
q is 0 and Q is a pyrydinyl group;
X is O, S or $NR^7$;
s is 0, 1, 2, 3 or 4;
each $R^{10}$ is independently hydrogen, $SR^7$, $OR^7$, amino, —O$(C_1-C_6)$alkyl, —$(C_6-C_{12})$aryl or halo; $X^3$ is absent, O, S, $C(R^7)_2$ or $NR^7$;
t is 0, 1, 2, 3, or 4;
each $R^9$ is independently hydrogen, $SR^7$, $OR^7$, amino, —O$(C_1-C_6)$alkyl, —$(C_6-C_{12})$aryl or halo; and
$R^{11}$ is hydrogen, $(C_1-C_6)$alkyl or $(C_6-C_{12})$aryl-$(C_1-C_6)$alkyl; or
$R^{11}$ is absent when the nitrogen to which $R^{11}$ would otherwise be attached, is attached to Q; or
an $R^{10}$ and an $R^9$ group, together with the atoms to which they are attached, form an substituted or unsubstituted ring; or
two adjacent $R^9$ groups, together with the atoms to which they are attached, form a substituted or unsubstitued $(C_6-C_{12})$aryl or a $(C_4-C_{12})$heterocyclyl.

7. A method of causing effective attenuation of colon carcinogenesis in a patient, comprising administering to the patient an effective dose of a compound of formula (III):

(III)

and pharmaceutically acceptable salts thereof, wherein:
n is 0, 1 or 2;
each $R^2$ is independently hydrogen, $(C_1-C_6)$alkyl, $(C_1-C_6)$ haloalkyl, $SR^7$, $OR^7$, amino, —O$(C_1-C_6)$alkyl, —$(C_6-C_{12})$aryl or halo X is O, S or $NR^7$, wherein $R^7$ is hydrogen or $(C_1-C_6)$alkyl;
$X^5$ and $X^6$ are each, independently, N or CH; and
$R^3$ is $(C_3-C_{12})$cycloalkyl, $(C_6-C_{12})$aryl, $(C_3-C_8)$heteroaryl or fused $(C_6-C_{12})$aryl-$(C_5-C_{12})$cycloalkyl.

8. The method of claim 7, wherein the compound of the formula (II) is a compound of the formula (V) or (VI):

(V)

and pharmaceutically acceptable salts thereof, wherein:
$X^1$ is N or CH;
$X^2$ is O, NH or S; and
$R^5$ and $R^6$ are each, independently, $(C_1-C_6)$alkyl, $(C_3-C_{12})$ cycloalkyl, $(C_6-C_{12})$aryl or, $R^5$ and $R^6$, together with the nitrogen to which they are attached, form a $(C_4-C_{12})$heterocyclyl group which, in turn, is optionally substituted.

9. A method of causing effective attenuation of colon carcinogenesis in a patient, comprising administering to the patient an effective dose of a compound of formula (VII), (VIII), (IX), (X), (XI) or (XII):

(VII)

(VIII)

(IX)

(X)

(XI)

(XII)

and pharmaceutically acceptable salts thereof, wherein:
d is 0, 1 or 2;
m is 0, 1 or 2;
each $R^2$ is independently hydrogen, $(C_1-C_6)$alkyl, $(C_1-C_6)$ haloalkyl, $SR^7$, $OR^7$, amino, —O$(C_1-C_6)$alkyl, —$(C_6-C_{12})$aryl or halo;
$X^1$ is N or CH;
$X^2$ is O, NH or S;
$R^3$ is $(C_3-C_{12})$cycloalkyl, $(C_6-C_{12})$aryl, $(C_3-C_8)$heteroaryl or fused $(C_6-C_{12})$aryl-$(C_5-C_{12})$cycloalkyl;
each $R^4$ is independently hydrogen, $SR^7$, $OR^7$, amino, —O$(C_1-C_6)$alkyl, —$(C_6-C_{12})$aryl or halo;

$R^5$ and $R^6$ are each, independently, $(C_1-C_6)$alkyl, $(C_3-C_{12})$cycloalkyl, $(C_6-C_{12})$aryl or, $R^5$ and $R^6$, together with the nitrogen to which they are attached, form a $(C_4-C_{12})$heterocyclyl group which, in turn, is optionally substituted; and $R^7$ is hydrogen or $(C_1-C_6)$alkyl.

10. A method of causing effective attenuation of colon carcinogenesis in a patient, comprising administering to the patient an effective dose of a compound of formula

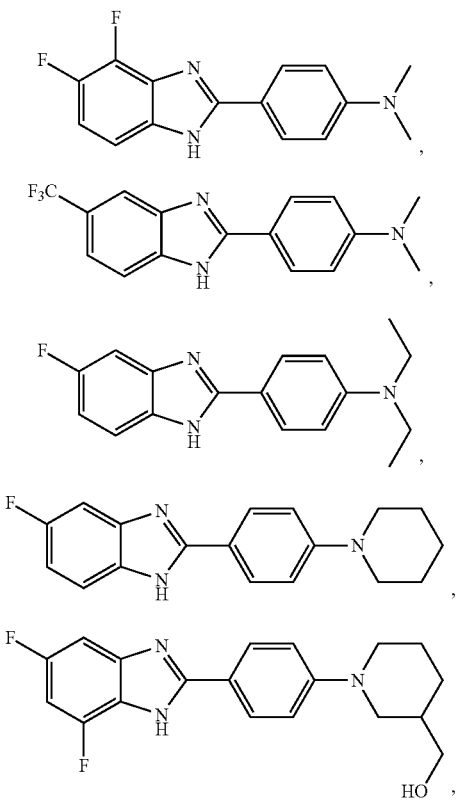

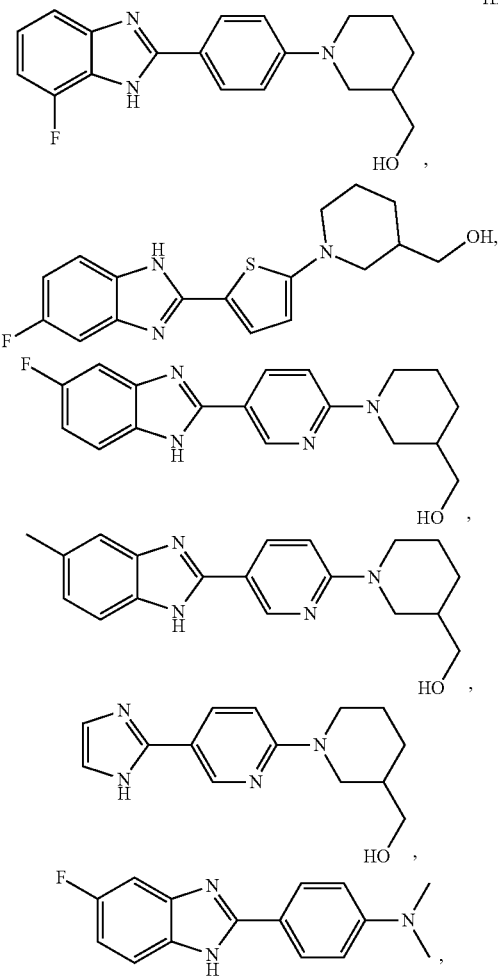

or pharmaceutically acceptable salts thereof.

* * * * *

UNITED STATES PATENT AND TRADEMARK OFFICE
CERTIFICATE OF CORRECTION

PATENT NO. : 9,616,047 B2  
APPLICATION NO. : 14/788373  
DATED : April 11, 2017  
INVENTOR(S) : Bode et al.

Page 1 of 3

It is certified that error appears in the above-identified patent and that said Letters Patent is hereby corrected as shown below:

On the Title Page

In item (72), in "Inventors", in Column 1, Line 2, delete "TX" and insert --MN-- therefor In item (72), in "Inventors", in Column 1, Line 4, delete "TX" and insert --MN-- therefor In item (73), in "Assignee", in Column 1, Line 1, after "Regents of", insert --the--

In the Specification

In Column 2, Line 17, delete "CO2" and insert --$CO_2$-- therefor

In Column 2, Line 38, delete "ofβ-catenin." and insert --of β-catenin.-- therefor In Column 5, Line 12, delete "HI-B 16" and insert --HI-B16-- therefor In Column 5, Line 21, delete "HI-B 16" and insert --HI-B16-- therefor In Column 5, Line 22, delete "HI-B 16" and insert --HI-B16-- therefor In Column 5, Line 60, delete "R1" and insert --$R^1$-- therefor In Column 6, Line 22, delete "R1" and insert --$R^1$-- therefor In Column 15, Line 19, delete "N(R)SO$_2$N(R')$_2$," and insert --N(R')SO$_2$N(R')$_2$,-- therefor In Column 17, Line 5 (Approx.), delete "R$_2$" and insert --$R^2$-- therefor In Column 17, Line 5 (Approx.), delete "R$_2$" and insert --$R^2$-- therefor Signed and Sealed this  
Second Day of October, 2018

Andrei Iancu  
*Director of the United States Patent and Trademark Office*

CERTIFICATE OF CORRECTION (continued)
U.S. Pat. No. 9,616,047 B2

In Column 17, Line 10 (Approx.), delete "$R_1$" and insert --$R^1$-- therefor

In Column 17, Line 10 (Approx.), delete "$R_1$" and insert --$R^1$-- therefor

In Column 17, Line 18 (Approx.), delete "$R_2$" and insert --$R^2$-- therefor

In Column 17, Line 18 (Approx.), delete "$R_2$" and insert --$R^2$-- therefor

In Column 17, Line 43-49 (Approx.), delete " 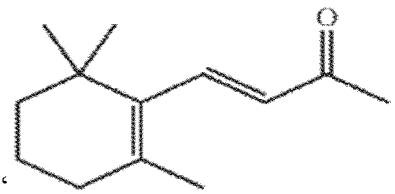 " and insert

-- 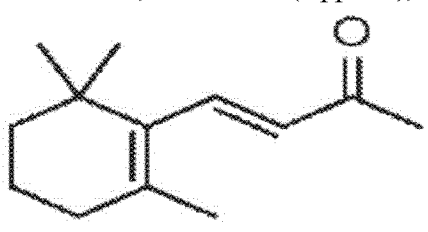 -- therefor

In Column 17, Line 57-66 (Approx.), delete " 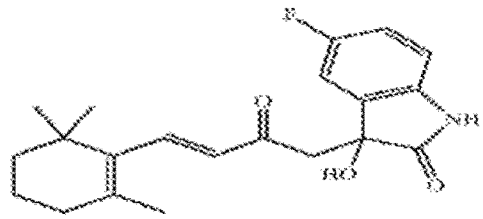 " and insert

-- 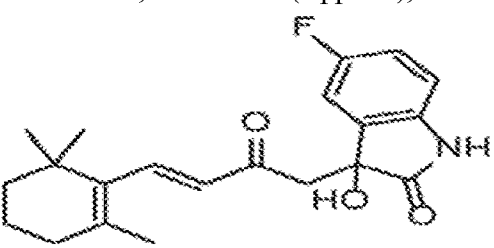 -- therefor

In Column 18, Line 26-35 (Approx.), delete " 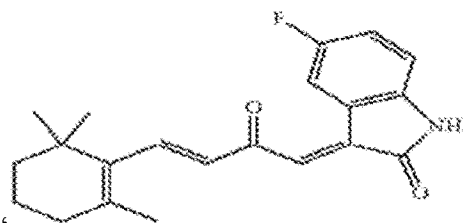 " and insert

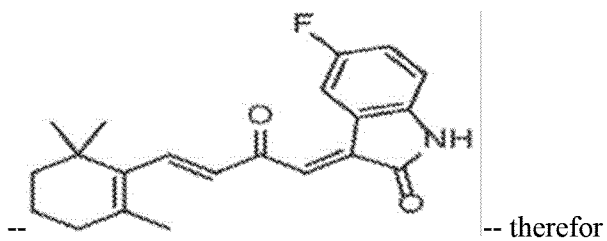 -- therefor

In Column 19, Line 22, delete "HI-B 16" and insert --HI-B16-- therefor

In the Claims

In Column 21, Line 51-52, in Claim 1, delete "($C_4$-$C_{12}$) heterocyclyl" and insert --($C_4$-$C_{12}$)heterocyclyl-- therefor In Column 21, Line 63, in Claim 1, after "halo;", insert --¶--

In Column 21, Line 66, in Claim 1, delete "$SR^7$ ," and insert --$SR^7$,-- therefor In Column 22, Line 27, in Claim 2, delete "$SR^7$,$OR^7$," and insert --$SR^7$, $OR^7$,-- therefor In Column 23, Line 6, in Claim 4, delete "N" and insert --$X^1$-- therefor In Column 23, Line 34, in Claim 4, delete "$SR^7$,$OR^7$," and insert --$SR^7$, $OR^7$,-- therefor In Column 25, Line 13-14, in Claim 6, delete "($C_4$-$C_{12}$) heterocyclyl" and insert --($C_4$-$C_{12}$)heterocyclyl-- therefor In Column 25, Line 24, in Claim 6, after "halo;", insert --¶--

In Column 26, Line 32, in Claim 9, delete "N" and insert --$X^1$-- therefor

In Column 27, Line 9, in Claim 10, delete "formula" and insert --formula:-- therefor